(12) United States Patent
Klein

(10) Patent No.: US 6,315,955 B1
(45) Date of Patent: Nov. 13, 2001

(54) METHOD AND APPARATUS FOR QUANTITATIVE PARTICLE DETERMINATION IN FLUIDS

(75) Inventor: Cornelis Klein, Hamilton (NZ)

(73) Assignee: DeLaval International A.B., Tumba (SE)

( * ) Notice: Subject to any disclaimer, the term of this patent is extended or adjusted under 35 U.S.C. 154(b) by 0 days.

(21) Appl. No.: 08/930,144
(22) PCT Filed: Apr. 1, 1996
(86) PCT No.: PCT/SE96/00424
§ 371 Date: Jan. 16, 1998
§ 102(e) Date: Jan. 16, 1998
(87) PCT Pub. No.: WO96/31764
PCT Pub. Date: Oct. 10, 1996

(30) Foreign Application Priority Data

Apr. 6, 1995 (NZ) .................................................. 270877
May 22, 1995 (NZ) .................................................. 272177

(51) Int. Cl.[7] .................................................. G01N 33/00
(52) U.S. Cl. .................. 422/73; 422/82.05; 422/82.09; 436/164; 356/317; 356/337; 356/338; 356/340; 356/343; 356/432; 356/435; 356/436; 356/441; 356/442
(58) Field of Search .................. 422/68.1, 73, 82.05, 422/82.09; 436/10, 63, 164; 356/300, 311, 317, 337, 338, 340, 342, 343, 432, 433, 435, 436, 441, 442, 445, 448

(56) References Cited

U.S. PATENT DOCUMENTS 3,547,540   12/1970   Shigemoto ........................... 356/28
3,552,855   1/1971    Crosswy et al. ..................... 356/28
4,348,111   9/1982    Goulas et al. ..................... 356/336
4,352,558   10/1982   Eisert ............................. 356/39
4,387,993   6/1983    Adrian ............................ 356/336
4,871,251   10/1989   Preikschat et al. ................. 356/336
4,957,363   9/1990    Takeda et al. ...................... 356/73
5,033,852 * 7/1991    Zaglio ............................ 356/339
5,260,584   11/1993   Popson et al. ................... 250/559.01
5,392,114   2/1995    Cole ............................. 356/338
5,416,580 * 5/1995    Trainer ........................... 356/336
5,416,581   5/1995    Kanngiesser ....................... 356/343

FOREIGN PATENT DOCUMENTS 681747     5/1993    (CH) .
63061144   3/1988    (JP) .
206602     5/1987    (NZ) .
226895     7/1990    (NZ) .
226896     7/1990    (NZ) .
1366922    1/1988    (SU) .
1784880    12/1992   (SU) .

* cited by examiner

Primary Examiner—Maureen M. Wallenhorst
(74) Attorney, Agent, or Firm—Hovey, Williams, Timmons & Collins

(57) ABSTRACT

The present invention includes a method and an apparatus for the quantitative determination of particles in fluid. The apparatus of the invention includes an emitters set of one or more light emitters, in combination with a detector set of one or more light detectors sensitive to the output of the emitters. During analysis of the sample, data from a plurality of signal paths between the emitter and detector sets are gathered. This information is subsequently evaluated by comparison with known data for different fluid particle contents. Some differentiation between different particles in a fluid sample are possible in many embodiments. Typical uses include analysis of milk and dairy fluids, blood samples, lubricants, suspensions of pigments, etc.

38 Claims, 10 Drawing Sheets

SECTION A-A

METHOD AND APPARATUS FOR QUANTITATIVE PARTICLE DETERMINATION IN FLUIDS

BACKGROUND OF THE INVENTION

1. Field of the Invention

The present invention is directed to a method and apparatus for the quantitative determination of particles in fluids. The preferred embodiments will find use for quantitative analysis of fat in milk and other dairy fluids.

2. Description of the Prior Art

The present invention is directed to the field of quantitative determination of particles in fluids. The term particle shall be used in its broadest sense and shall typically not only be restricted to mean pieces of solid matter in another phase, but also include the situation of small volumes of liquid in another liquid phase—an example would be micelles or small globules dispersed in a bulk liquid phase such as in an emulsion, or fat globules in a liquid such as milk.

In addition, the term 'fluid' shall also be taken to include the gaseous phase though it is envisaged that most embodiments will be used in applications where the fluid is a liquid.

Most apparatus which is currently used for the quantitative determination of particles in a fluid are relatively complex in nature. Their degree of complexity is at least partially a cause for several disadvantages:

they are relatively expensive;

they are often relatively delicate and generally unsuitable for use in the field or in normal manufacturing and processing environments;

they are generally specific in purpose and often cannot be readily adapted for other applications;

they are often unable to be used for monitoring an in-line sample arrangement—most embodiments require samples to be removed from the production line and placed in the apparatus for analysis.

Much of the art relies on spectroscopic techniques for quantitative determination of particle presence in a fluid. Most of these techniques are based on infrared spectroscopy and are only useful in many cases for detecting and quantitatively determining organic or organometallic particles in the fluid. An example is the subject matter of NZ Patent No. 192325 which describes a method of quantitative measurement of fat in a sample by using an infrared absorption technique and evaluating the infrared absorption characteristic of saturated carbon-hydrogen bond stretching. However this and corresponding methods are generally specific to the quantitative analysis of particular categories of compounds and could be influenced by the presence of substances other than those of interest which are also present in the sample.

International Patent Appln No. WO 92/17767 is directed to a similar method of quantitative fat determination in an emulsion and also takes into account infrared absorption peaks due to other (than C—H bond excitation) as well. While this technique would also appear to improve selectivity (and thus have the potential to eliminate interference from other substances present in the sample) it also claimed that more accurate determinations can be carried out directly from full milk, without a preceding homogenisation treatment. However the invention described in this specification also possesses many of the general disadvantages described above.

French Patent No. FR 2050525 describes a method where an infrared beam is reflected off parallel transparent walls bounded on the outside by the sample fluid. Here only part of the beam will be reflected (and some absorbed or transmitted through the sample liquid) to be measured as it exits the chamber. The intensity of the reflected beams reflects particle content, supposedly. However this method will have limitations in the number and type of different fluids with which it may be used.

Russian Patents Nos. SU 983538 and SU 1748058 are also directed to methods of particle determination in fluids though rely upon the use of expensive or complex equipment; one of which prefers the use of a maser which is not an off-the-shelf item in most countries.

In general the bulk of the prior art does not allow for the continuous or in-line monitoring of sample fluid and are generally and relatively inflexible in how they may be used or applied.

It is an object of the present invention to address the foregoing problems or at least to provide the public with a useful choice.

Further aspects and advantages of the present invention will become apparent from the ensuing description which is given by way of example only.

SUMMARY OF THE INVENTION

According to one aspect of the present invention there is provided apparatus for quantitative particle determination in fluids, said apparatus comprising:

an emitter set comprising one or more light emitters in turn providing one or more sample light signals;

a detector set comprising one or more light detectors sensitive to the output of the light emitters, the arrangement being characterised such that the sample light signals from a plurality of sample light signal paths between the emitter and detector sets are received by the detector set during analysis of a sample;

the detector providing output values which can be evaluated by processing means for providing a value indicative of the fluid particle content.

According to another aspect of the present invention there is provided apparatus, substantially as described above, in which the detector set is arranged to detect at least one set of scattered or reflected light signals due to reflectance by particles present within the fluid.

According to another aspect of the present invention there is provided apparatus, substantially as described above, which includes optical feedback means comprising a feedback detector whose output provides for at least one of:

influencing either or both the voltage and current of at least one light emitter to maintain light output at a predetermined level;

influencing the sensitivity of at least one light detector to match the light output of at least one light emitter, and providing a signal available to processing means for use in correction when providing a value indicative of particle content.

According to another aspect of the present invention there is provided apparatus, substantially as described above, in which said sample light signal paths differ from each other by at least one of:

their path length through the fluid sample being analysed, and their relative path angle through the fluid sample being analysed.

According to another aspect of the present invention there is provided apparatus, substantially as described above, comprising an emitter set comprising a plurality of light emitters at different positions along the wall or walls of a sample cell, or positioned to be present along the wall or walls of an inserted sample cell; the output of said emitters directed to provide a plurality of substantially direct signal paths to one or more light detectors of the detector set.

According to another aspect of the present invention there is provided apparatus, substantially as described above, comprising a plurality of pulsed light emitters, and in which the detector set, or an individual detector of the detector set, detects substantially the output of a single light emitter, or combination thereof, at a time during analysis of a sample; the pulsing of said light emitters being synchronised to allow the detection of the output of individual light emitters, or groups thereof.

According to another aspect of the present invention there is provided apparatus, substantially as described above, which includes processing means which compares values produced by the detector set with stored calibration reference values, the comparison producing values indicative of the presence of one or more different types of particles within a sample fluid.

According to a further aspect of the present invention there is provided a method for the quantitative determination of the levels of one or more different particles in a fluid comprising transmitting one or more light signals into a fluid sample, detecting the sample light signals from a plurality of sample light signal paths, and making the detected output available for subsequent evaluation by processing means.

According to another aspect of the present invention there is provided a method, substantially as described above, in which the detected light signals differ by at least one of the following:

their path length through the fluid sample being analysed;

their relative path angle through the fluid sample being analysed;

the output intensity of the emitter producing said signal;

the proportion of transmitted to reflected or scattered light, and wavelength.

According to another aspect of the present invention there is provided a method, substantially as described above, in which the detected output is compared by either or both or linear regression, and Fourier transform analysis, with stored calibration reference values to produce values indicative of the quantitative levels of one or more different types of particles within said fluid.

According to another aspect of the present invention there is provided a method, substantially as described above, for the determination of particle levels for at least one of:

milk and other dairy based fluids;

substances containing fluidised fat particles, globules, and suspensions;

blood, plasma, semen, urine and other biological fluids;

oils and lubricants, and inks, paints, and liquid pigments.

According to another aspect of the present invention there is provided a method, substantially as described above, when applied to milk and other dairy based fluids, the method being used to indicate the levels of at least one of: fat, protein, lactose, and somatic cell count.

The present invention may be generally characterised by obtaining and comparing values for a plurality of light signal paths through a fluid. The considered signal will differ in a number of physical characteristics rather than comprising repetitions of a signal through the same path. This does not, however, preclude obtaining multiples of data from a signal along the same path—only that this should not be the only path considered for analysis.

The manner by which the signal paths differ can vary. For instance, paths may differ in the following manners:

their path length through the fluid sample being analysed;

their relative path angle through the fluid sample being analysed, whether the emitted light beam is directly incident upon the detector.

Earlier embodiments preferred sample analysis by obtaining substantially different values for both reflected and transmitted light through a sample. However, multiple signal paths through a sample and which are incident upon a detector will also give rise to a component of scattered and reflected light, due to particle presence in the sample, which will also be normally observed by the detector. Accordingly the separate acquisition of transmitted and reflected data for subsequent combination and evaluation can be substituted in many embodiments by merely obtaining detection values for a range of different transmitted signal paths. For many fluids it is perhaps preferable that these paths have different relative angles, as this will often cause the various signal paths (when reaching the detector) to comprise different proportions of transmitted to reflected/scattered light.

It is envisaged that while preferred embodiments of the present invention shall be directed to the determination of fat in milk and other fluids, the present invention may also be applied for the determination of particles in fluids such as emulsions and suspensions, inks, blood, as well as hydraulic, machinery and other types of oils etc.

It has been found from trials that the same apparatus may be used to determine, or at least provide a reasonable approximation of, the levels of different particles in a fluid. This appears to depend upon the fact that different types of particles exhibit different degrees of absorption and reflectance (often as well as different angles of reflectance/scattering). The signals collected from a detector set will be a function of the combination of each constituent's reflectance and absorption characteristics. By comparison with reference values, the contribution of each constituent particle type can be determined and by further mathematical analysis, a quantitative value obtained. For example, for a fluid such as milk, reasonable indications of the levels of lactose, fat, protein, as well as the somatic cell count, can be obtained as well as total particle presence.

As most practical embodiments of the present invention are relatively simple and may be constructed to be relatively rugged in design, perhaps on a single board or module, various embodiments of the present invention may find use in the continual monitoring of milk and other fluids. The continuous or periodic monitoring of lubrication fluids in situ is one example of the practical use of certain embodiments of the present invention. Here embodiments of the present invention may be used to sound an alarm or shut down machinery if the presence of particles exceeds a predetermined value. Use in engines in the automotive and aviation field is an example of one specific use. Use for blood, plasma, semen, urine and biological fluid analysis are some other applications. Use with inks, paints and pigments are some others. In practice the invention can be applied to virtually any fluid in which there are present particles able to interact with a light signal. This may be at low levels, suggesting uses in quality control applications such as purification equipment, monitoring the clarity of fluids such as water, as well as fluid feed lines in industrial plant, and so on.

Most embodiments of the present invention will operate in the infrared region though other regions of the electromagnetic spectrum may also be relied upon. Preferred embodiments operate in either or both of the 750–1200 nm and 3000–10000 nm wavelength regions (both in the infrared region). Inexpensive emitters, such as light emitting diodes (LED's), are readily available for the infrared and visible regions. Other types of light emitters may also be relied upon.

Similarly, relatively inexpensive light responsive detectors whose light output is dependent upon the incident light are also available. Many of these are also relatively sensitive to within the infrared region and the proliferation of infrared remote control units has ensured that matched diodes and detectors are readily, and inexpensively, available. However it is noted that various types of light sensitive detectors may be used in various embodiments of the present invention. These may, for instance, comprise photo diodes, light emitting diodes (LEDs), photo transistors, and other optoelectonric devices. In some cases the use of more sophisticated or sensitive detectors may be justified for many applications relatively inexpensive devices may suffice.

It has been previously mentioned that the method of operation of the present invention involves a comparative analysis based on obtained values for a sample which includes some information on light transmittance and reflectance by the sample. As also previously mentioned, this information need not be gathered separately but may be included in a single reading from a detector, though preferably there should be a number of different signal paths to ensure a reasonable degree of accuracy. These factors will have a bearing on the number and manner by which the emitters and detectors used in an embodiment of the present invention are arranged. A number of possibilities exist and will now be discussed by way of example.

Typically, a working embodiment of the present invention will comprise at least one emitter set and one detector set. For simplicity of description, reference shall be made, unless otherwise stated, to a single emitter set and a single detector set.

Each emitter set may comprise one or more light emitters. Similarly, the detector set may comprise one or more light detectors. The emitter set and detector set shall be generally arranged so that both transmitted and reflected light values may be obtained, though not necessarily concurrently. Several examples, in which transmittance and reflectance data can be obtained separately for subsequent processing/ evaluation follow:

One particular arrangement would be to have a single light detector, or an array of several light detectors which function more or less as a single light detector. In combination with the single light detector would be at least two light emitters. At least one of these light emitters could be arranged so that its sample light signal would be received as a transmitted light signal by the light detector i.e. the sample light signal would travel directly through the sample fluid to the detector. At least one other light emitter would be arranged so that a reflected signal was received by the light detector. If we consider of the simple example of the sample fluid contained in a cell between two windows, at least one of the emitters will be on the same side of the sample cell as the light detector (though typically displaced by a distance along the cell window therefrom), while the other light emitter would be positioned so that its signalled passed through the opposite cell window. Such a situation is illustrated in FIG. 1 of the specification.

In another arrangement, there may be provided only a single light emitter and at least two light detectors. At least one of the light detectors will be positioned to receive transmitted light from the light emitter while at least one other will be positioned to receive reflected light. Such an arrangement is illustrated in FIG. 2.

In other arrangements, there may be a plurality of both light emitters and light detectors. Each detector (and also in the instance where the detector set comprises a single light detector) may receive light from a plurality of light emitters. This may comprise a plurality of reflected signals from different light emitters. This may also comprise a plurality of transmitted signals from different light emitters. The arrangement may also comprise one or more each of transmitted light signals and reflected light signals per detector.

It is envisaged that for the arrangement of the preceding paragraph, not all light signals for a particular light detector shall be received concurrently. In most instances it is envisaged that the signals will be sequenced from the different emitters with which a particular light detector will interact. Concurrent sequences between different detector and emitter pairs/sets may take place in some embodiments.

It is possible that different light detectors may also react to the signals from a single light emitter in operation—for these light detectors the path lengths may be different (for transmitted signals) or at different angles for reflected signals. As can be appreciated other arrangements of emitters and detectors may also be set up.

In other embodiments where purely reflected readings are not taken, the detector and emitter sets will be arranged to allow a plurality of readings of signals from different paths to be obtained. This may allow the use of a number of emitter and detector combinations, including at least some of those combinations mentioned above and below. However the arrangement in such embodiments will typically be such that most, is not all, of the detectors will receive a transmitted signal, though a portion of light falling upon the detector being due to scattering/reflectance by particles within the fluid. Reflectance and scattering will also contribute to absorbance, so that in practice a plurality of signal paths differing in length and/or relative angle has been found sufficient to allow quantitative particle evaluation. In practice from 3–5 different path lengths has been found a satisfactory compromise between excessive complexity and accuracy. Depending on the sample and other parameters, from 2 paths upwards may be relied upon.

Altering the intensity along each path, to obtain readings for different intensities, can also be incorporated into various embodiments. This increases the different types of data collected in sample analysis, and can increase accuracy or certainty in some instances e.g. for some types of fluids, and for some types of particles.

As can be appreciated there are a number of various possible arrangements of emitters and detectors to provide the plurality of different types of data (e.g. resulting from different signal and path characteristics) preferred for accurate sample analysis. Other arrangements than thus far specifically mentioned may be set up to cover one or more of the following situations:

where a plurality of emitters concurrently work and act in conjunction with a plurality of light detectors on a one to one basis, and where each signal path is substantially identical in characteristics so that a range of supposedly identical readings are simultaneously obtained for averaging or other comparison;

the situation where a single emitter acts with several detectors concurrently on a one to many basis, and where the physical signal path characteristics (e.g. path lengths, angles etc.) are substantially identical so that the values obtained may be averaged or otherwise compared;

the situation of the preceding paragraph wherein the characteristics of the signal paths from the emitter to each detector differs so that a range of different signal path values may be obtained for subsequent evaluation;

where a single light detector may concurrently receive light from a plurality of light emitters, the signal path from each light emitter to the single light detector being substantially identical so the values may be averaged or otherwise compared;

the situation of the preceding paragraph in which each emitter to detector signal path differs.

It should also be envisaged that by sequencing, pulsing or otherwise providing non-continuous operation of the emitters and/or detectors, different combinations of emitters and detectors may be selected during a data gathering cycle.

While in some embodiments, if there are sufficient light emitters and light detectors, the operation of the emitter and detector sets may be substantially continuous, it is envisaged that pulsed or non-continuous operation may commonly be used. This may provide a number of potentially realisable advantages. For instance, sequencing or synchronising the operation of different light emitters and light detectors can allow the data for a number of different signal path lengths to be obtained. The apparatus may cycle through sequences of such data gathering steps to obtain an extended data set for subsequent comparison and evaluation. This information may provide enhanced or more consistent values for the quantitative determination of particle presence especially if the sample is not homogenous, or flowing. As can be appreciated, different data gathering cycles need not be identical in their sequence, or number of data gathering steps for that cycle.

Another potentially realisable advantage of non-continuous operation is in reducing the energy (over time) required by the light emitters. This may be a consideration in remotely installed units, or where there is a requirement for economy of power. Alternatively, many light emitting devices allow for higher than normal operating currents for short periods of time. This would allow for higher intensity bursts of sample light signal than would be possible if the light emitting device was operated continuously within its normal operating parameters. This may improve the operation of the apparatus, perhaps make it amenable to a higher range of sample types, and also perhaps improve economy by allowing the use of lower rated of components than if the apparatus was operated continuously.

Various other modifications may be made to the apparatus. These modifications may in some instances improve accuracy, consistency, or the ability to analyse difficult samples. In some instances the modifications may just be an alternative to some of the foregoing arrangements. One modification is to modulate the intensity of a sample reference beam. In many ways this is analogous to obtaining readings at different path lengths (at the same angle) through the sample fluid and may be used as an approximation for such. The data will not always be exactly equal to the results of different path lengths, though will still be able to provide information characteristic of a particular sample, or samples.

In some embodiments information regarding the intensity will also be supplied, with the detector response, to data logging/comparison means so that any comparative analysis can correlate the results with the output of this sample beam emitter.

Modification of the output intensity of the sample light emitter can also be used to autorange the output to match the characteristics of the detector. In such a situation the machine can adjust itself (though this may be performed manually) so that the detector is operating within its most efficient or accurate region. An alternative would be to adjust the output intensity so that the signals received by the detector are within a comparable range to that of the output or calibration data already stored for the particular sample type.

Another type of operation is also possible. Rather than providing a fixed, known sample beam intensity, the intensity could be altered until the detector receives a particular signal strength. The intensity of the outputted sample beam to achieve that intensity can be used for subsequent analysis. Such information may also be combined with a sample data set obtained using a constant known intensity sample beam. The gathering, comparison and analysis of data collected, for a particular sample, by different measuring techniques can be useful in increasing the accuracy, or consistency of the apparatus. This may be useful where different types of sample, or a large variation of sample characteristics, are encountered by the apparatus of the present invention.

While the intensity of the sample beam could be gathered at the source, it is envisaged that some other characteristics of the light emitting device will be measured instead. For instance, for a device such as an LED, the current passing through the device may be used as an indication of intensity. Calibration of a particular light emitting device to correlate its output intensity with current drawn (or some other characteristic (such as voltage etc.)) is a possibility. However where sample results are matched with calibration data, the exact output intensity need not be known as results are not obtained by absolute values but by comparing the results with stored data taken through calibration runs under similar conditions. This will often depend upon the particular embodiment of the apparatus and whether recorded or calibration data is relied upon. In most cases however, it is desirable that the characteristics of the light emitting device, and also other components of the apparatus, are relatively consistent, and resistant to drift—at least during the period of any trial, or between calibration runs. This can be a problem in some applications of the invention and may be addressed by optical feedback means, which will be discussed further below.

Another technique which may be employed is to alter the direction of the emitted sample beam. It is envisaged that this technique is more likely to be used where an emitted beam is a substantially narrow beam, rather than a broad beam which can be monitored from a number of different positions anyway. Altering the angle of the beam is another method of performing modulation. For a particular fixed detector, altering the angle of the sample beam will have the effect of providing a different measured intensity which is dependent not only upon incident light (depending on the positioning of the detector) but also upon detecting different amounts of backscatter, reflection and absorption by the sample fluid. This provides a different type of information to merely modulating the sample beam intensity, and could be useful in a number of ways.

This information can again be matched with calibration or recorded data. It may also provide information on the nature of the particle content (e.g the reflectance, size, surface irregularity etc. of particles will all have a bearing on reflectance and backscatter) which may be able to provide additional information to the user. If the different forms of modulation and measuring outlined within this invention are also used, a more complete set of information for the sample can be obtained which may be useful in more accurately identifying not only the concentration or particle content, but also other characteristics of the sample. Measurement of different components within a sample, or the ratios of these components, may also be a possibility.

Physical features may also be provided to alter a sample beam characteristic. This may include the use of reflectors and lenses which interact with a sample beam. These may only interact with a portion of the sample beam. The use of reflectors, lenses, beam splitters, and filters are envisaged. The use of filters which can be altered in their characteristics are another means of modulating characteristics of the sample light source. The beam may then interact with the sample in different ways (the technique of altering the frequency of the sample light source has previously been discussed). Use of each of these devices are yet another way of altering the characteristics of the sample light beam so that the response of the sample fluid (to different measuring techniques) can be obtained and subsequently evaluated.

In some instances the light intensity output from an emitter may vary over time. This can affect the results of sample analysis, especially if other emitters, and detectors, do not drift identically. Even for LED's, a gradual lessening in output occurs over their life. The temperature of the fluid may affect the temperature of an emitter, detector, and other components leading to variations in readings, though typically the greatest influence will be upon the output intensity of the emitter. Due to stability problems, LEDs have generally been avoided, in analytical devices of this kind, by the prior art.

To address these problems use may be made of some form of feedback (referred to herein as 'optical feedback') to compensate for such drifts and variations. In a preferred embodiment an additional source detector is used to measure light intensity directly at the emitter source. Feedback from this detector then alters either or both of the input voltage or current to the emitter to ensure that its output intensity remains constant.

An alternative is to use information from the source detector to vary the sensitivity of the detector(s) to match the output intensity of the source. Another alternative is to use the feedback to provide further data to be taken into account during subsequent processing and evaluation of values/signals obtained by the detector. Combinations of these, and other techniques may be relied upon.

The nature of the source detector may vary. It may be similar or different to other detectors used within the apparatus. Some advantage may be obtained by using as a source detector, an emitter identical to that being monitored. Many emitters are able to be connected in a manner allowing them to function as a detector. Advantage may be obtained as such a source detector will react fairly similarly to the emitter in response to physical characteristics such as temperature etc. Further, an LED is often less expensive than a photo diode detector (used in many embodiments).

Physical modifications may also be made to isolate the sensitive components of the apparatus from physical influences such as temperature. Mounting the components in a mass of material exhibiting thermal inertia will help prevent rapid changes in temperature. Providing heat exchanging fins or features with the surrounding environment may help resist temperature changes due to the sample—providing the surrounding environment is relatively stable. Providing in-built temperature sensing to activate heating, or cooling means (e.g. a Peltier effect device), may be used in some embodiments. The information from temperature sensors could also be evaluated as part of sample analysis by the processing/evaluation means.

Thermally isolating the apparatus from the sample may be employed in some embodiments. Providing a physical air gap between the cell walls and apparatus is one method. Doubly insulated cells, perhaps evacuated between the walls, is a possibility though a double cell wall could introduce additional reflection and refraction. If this is constant, this influence may be eliminated by comparison with reference sample data collected with the same arrangement.

Other techniques and methods may be employed in various embodiments. Many applications may not require a high degree of accuracy, or merely need to determine rapid or significant changes in a sample being monitored. In these applications a high specific degree of accuracy may not be required, and a simple embodiment of apparatus without optical or other feedback may be sufficient.

The output response from the detector set will normally reflect particle presence in a sample fluid. However, as has been mentioned, in some instances other components or physical characteristics of the sample fluid may also affect the sample light signals and therefore the response from the detectors. In instances such as these several other techniques may be relied upon to provide a final value from the apparatus which is more indicative of the true level of particle presence in the sample fluid.

One technique which may be effective in certain situations is the use of a second, reference sample signal for comparison. In such cases the differences between the sample and reference are generally evaluated to provide the final output value of particle determination. Such techniques are well-known and will not be described in treater detail here.

It should be noted that the above arrangement will not always be suitable for all applications. In some instances it may not be physically possible or practical to provide a duplicate set of equipment. In other instances where in-line flow monitoring occurs, the nature of the monitored sample fluid may be continually changing so that it is difficult to obtain a 'typical' reference sample. In other instances the lifetime of a reference sample may be relatively short (e.g. a reaction intermediate) and thus it may not be practical to rely on a reference sample.

Another technique which may address some of the foregoing problems is to rely on collected data for comparison. This collected data may be collected from a variety of reference and calibration standards. Where the nature of the sample fluid is expected to change, additional sensing devices may be provided to determine the change in characteristics of the sample fluid (other than changes in particle concentration and presence), so the apparatus may subsequently determine which data set of stored reference and calibration standards most closely matches the physical characteristics of the sample fluid evaluation. However it is envisaged that such arrangements are more likely to find use for difficult or extreme cases.

It is envisaged that the present invention may be used for a wide range of fluids. Some typical fluids have been mentioned previously, and include substances such as blood, oils and lubricants, milk and other dairy products, fluidised gas/solid flows, inks, paints and pigments, etc. In some of these situations the fluids may be opaque to the chosen sample light signal and it may be necessary to rely on a sample light signal of a different wave length. In some instances it may be necessary to move outside of the infrared through visible light region of the electromagnetic spectrum. Other regions such as radio frequency, or the shorter microwave and X-ray bands may also be considered though the emitter and detector devices may be substantially more complex—this may negate some of the potentially realisable advantages of the present invention such as simplicity and lower cost. However, in some situations, relying upon sample signals in other regions of the electromagnetic spectrum may be preferable, or superior, to other currently available techniques.

It is also possible in some embodiments that there is an option to alter or vary the nature sample light signal—this includes frequency, intensity etc. This could be provided by additional sets of emitters which can be selected either automatically, or by user preference. The use of emitters whose output frequency can be varied, or which emit over a range or number of frequencies which can be selectively filtered, may also be provided. Emitter controlling devices which can alter the output of an emitter can also be relied upon.

As a further enhancement in some embodiments of the present invention, use may be made of varying sample light frequencies for scanning/analysis of the sample fluid. While, for substances such as milk, reasonable results may be obtained with a single frequency sample light signal, scanning the sample at several different frequencies may improve results in some instances. Where particles are opaque, or at least partially so, to the sample light signal then their interaction with different sample light signal frequencies should theoretically be the same. Interference by other components in the sample fluid may, in contrast, have varying effects on different frequencies. By suitable analysis and comparison of the detector responses at different frequencies, a clearer picture can be obtained of the effect of just the presence of particles on the detector output. It is envisaged however that such modifications will not necessarily be used in all embodiments though for some sample fluids it may be desirable, or necessary, to incorporate such improvements.

In most embodiments of the present invention the output responses of the detector set will be considered and evaluated to produce a value indicative of the quantity of particles in the sample. This evaluation will generally be performed by some form of processing device, typically electronic. Such a device may be incorporated into the apparatus though the use of an external processing device such as a computer is another typical scenario.

In most instances it will be necessary to convert the output from the light detectors to a form suitable for subsequent evaluation or processing. In many embodiments an analog to digital converter will be relied upon to provide the required conversion. It should be appreciated however that various other techniques are capable of converting the output of the detector set into a format with signals suitable for subsequent evaluation or determination by any processing means which may be employed.

Subsequent evaluation of the data may be by a number of methods. Some trial and experimentation may be relied upon to determine the best method for obtaining values indicative of particle presence in the sample fluid. However, for ease of use most embodiments will rely upon the comparison of received signals with collected or stored data. This data may be values which have been pre-programmed into any processing apparatus (for simplicity of description the term 'processing portion' will be used to refer to a portion or apparatus relied upon to produce a final result from the output of the detector set, or converted signals therefrom) so that the subsequent collection of 'initial set-up' data by the user may not be required. This stored data may comprise values typical for the type of sample fluids to be analysed though it is envisaged for most embodiments that there will be provided provision for routine calibration using reference samples to either check accuracy and/or adjust the apparatus. This information will often be stored and could be stored in EPROM, or software being run by the processing portion. The use of software may be more flexible allowing for the updating of software to change the performance of the apparatus.

In a preferred option, reference is made to calibration data from reference standards which are stored in software. This information may be updated whenever a new calibration run has been done.

In most embodiments predetermined functions that are best suited for the sample fluid in question are relied upon to assist in eventual comparison and determination in particle presence. In a preferred embodiment a linear regression type technique is relied upon and for milk a logarithmic based function is generally applied to produce a straight line relationship between particle presence and detector response. It should however be appreciated that different detector characteristics (which may not necessarily be linear or logarithmic) will have an influence on any function required to adapt a response to a straight line such as required for linear regression. p Many mathematical techniques, and software, are available which can automatically modify data to fit a straight line, or which can select a suitable equation for the line. Use of such existing techniques is envisaged, as is envisaged the use of Fourier transform techniques. It is not necessary that the data fits a straight line, only that some pattern emerges enabling newly acquired data to be compared with the existing data to provide a value indicative of the concentration or quantitative presence of particles within the sample fluid.

In some instances the value delivered by the processing portion may be on an arbitrary scale, though it may also be modified to conform to an existing accepted scale, or even a user defined scale. Where the absolute percentage or concentration of particles in a fluid is not required, such as in the case where the user merely needs to monitor that particle presence in a sample fluid does not fall outside of predetermined limits, then an arbitrary or meaningless scale may be relied upon. In other instances the processing portion may deliver a value forming to an accepted scale or user chosen units combination (e.g. g/liter).

BRIEF DESCRIPTION OF DRAWINGS

Further aspects of the present invention will become apparent from the ensuing description which is given by way of example only and with reference to the accompanying drawings in which:

FIG. 6 is a plan diagrammatic view of the embodiment of FIG. 5.

FIG. 7 is a side diagrammatic view of the embodiment of FIGS. 5 and 6.

DESCRIPTION OF THE PREFERRED EMBODIMENTS

Figure 1A:
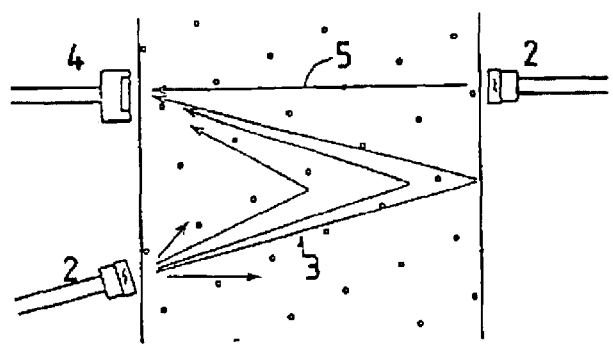
FIGS. 1a, 1b and 1c comprise side diagrammatic views of some embodiments of emitter and detector arrangements according to the present invention.

According to one embodiment of the present invention there is provided apparatus (generally indicated by arrow 1) for quantitative particle determination in fluids, said apparatus comprising:

an emitter set comprising one or more light emitters 2 providing one or more sample light signals (generally indicated by arrow 3,5);

a detector set comprising one or more light detectors 4 sensitive to the light of the sample light signal(s) 3,5;

the arrangement being characterised such that the sample light signals from a plurality of sample light signal paths 3, 5 between the emitter (2) and detector (4) sets are received by the detector set during analysis of a sample;

the detector (4) providing output values which can be evaluated by processing means (6) for providing a value indicative of the fluid (7) particle content.

EXAMPLE 1a

FIG. 1 illustrates one particular arrangement which has been discussed previously. Here there are a plurality of light emitters 2, one of which provides a substantially transmitted signal 5 to a light detector 4, and one of which provides a substantially reflected signal 3 to said light detector 4.

EXAMPLE 1b

Figure 1B:
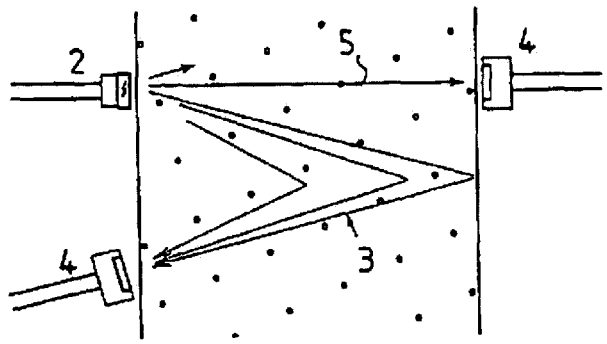

FIG. 1b illustrates another arrangement, also previously discussed, which comprises a single emitter 2 whose output sample light signal 3, 5 is received by a plurality of detectors 4, at least one of which is positioned to intercept transmitted light signal 5, and at least one other is positioned to detect reflected light signal 3.

Figure 1C:
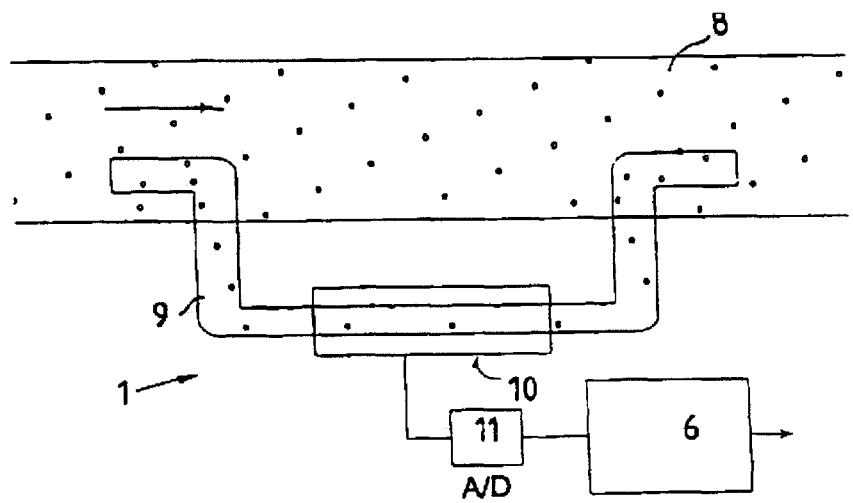
Figure 2:
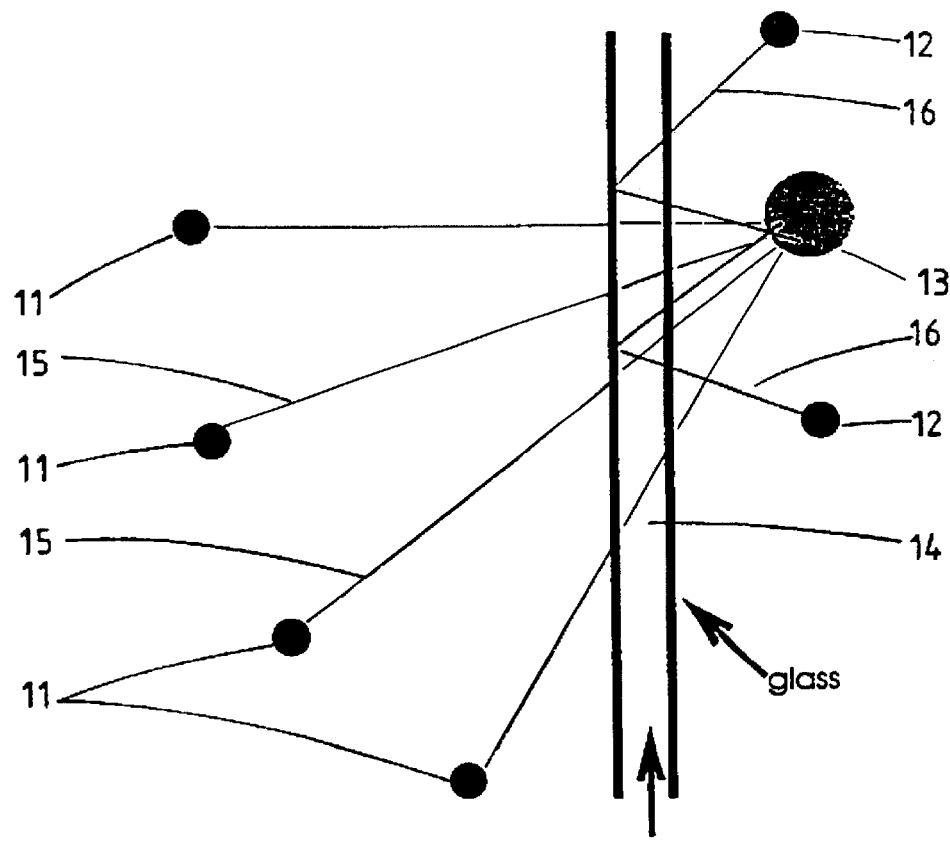
FIG. 2 is a side diagrammatic view of a possible embodiment of the present invention.

The transmitted light signals need not be direct as illustrated in FIGS. 1 and 2. It is possible that the detector 4 could be off-set with respect to the emitter 2, one effect of which would be to increase the path length. It is also possible that several detectors 4 are provided with differing path lengths from the associated emitter 2. It is also possible that a plurality of emitters (of which only one at a time would operate) could be provided to allow for the different detectors to each receive successive signals (from each emitter) having different transmission path lengths and/or angles.

Typically the transmitted path length 5 is relatively small. In one embodiment for measuring milk and dairy samples, the distance across the cell is approximately 0.5 mm. However this may alter according to the characteristics of the sample fluid and the emitters and detectors. In embodiments accepting a sample tube or phial.

While it is generally preferred that the sample fluid is stationery, movement of fluid is tolerated in most embodiments. It is envisaged that fluid velocities of up to 0.5 m per second $ms^{-1}$ may be tolerated. Higher velocities may also be tolerated in some instances. The main problem with fluid movement is that the characteristics may alter over time if the nature of the fluid alters. For instance air pockets, concentration gradients, turbulence etc. may have an effect on readings. One possible solution is the use of pulsed or non-continuous readings so that each data collection set comprises a series of snap shots which effectively freeze a moving fluid. For such embodiments relatively high fluid flow rates may be tolerated. Such strobe like techniques may also be used where chemical reactions are being monitored and where there are rapid or significant changes over a short period of time.

EXAMPLE 1c

FIG. 1c illustrates a possible practical embodiment of the present invention. Here there is main fluid line 8 from which a continuous sample is drawn via a bypass conduit 9. Restrictions may be provided in the conduit to slow the rate of fluid flow, at least in the sample analysing portion 10 containing the emitter and detector sets. The output of the detectors 4 is transmitted to a A/D converter whose output is then received by the processing portion 6.

EXAMPLE 1d

Figure 3:
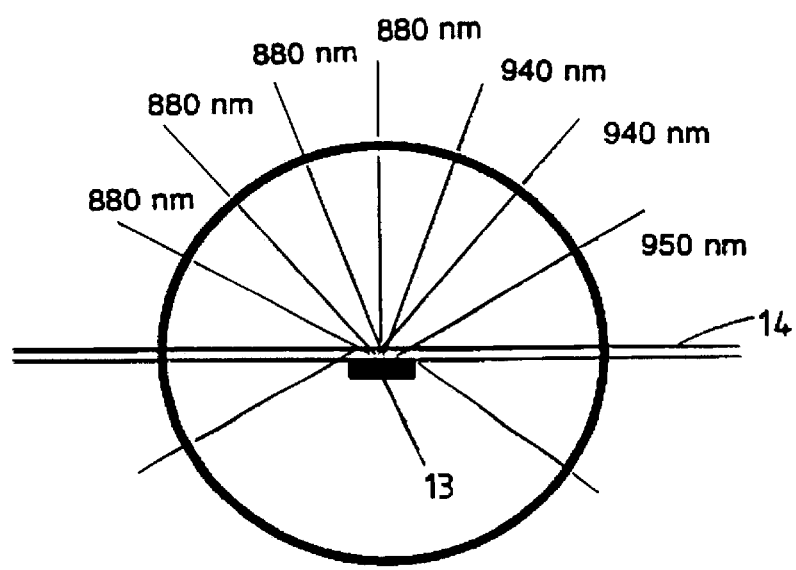
FIG. 3 is a diagrammatic view of an embodiment of a cell and possible wavelength allocation for an embodiment measuring at different light frequencies.
Figure 4:
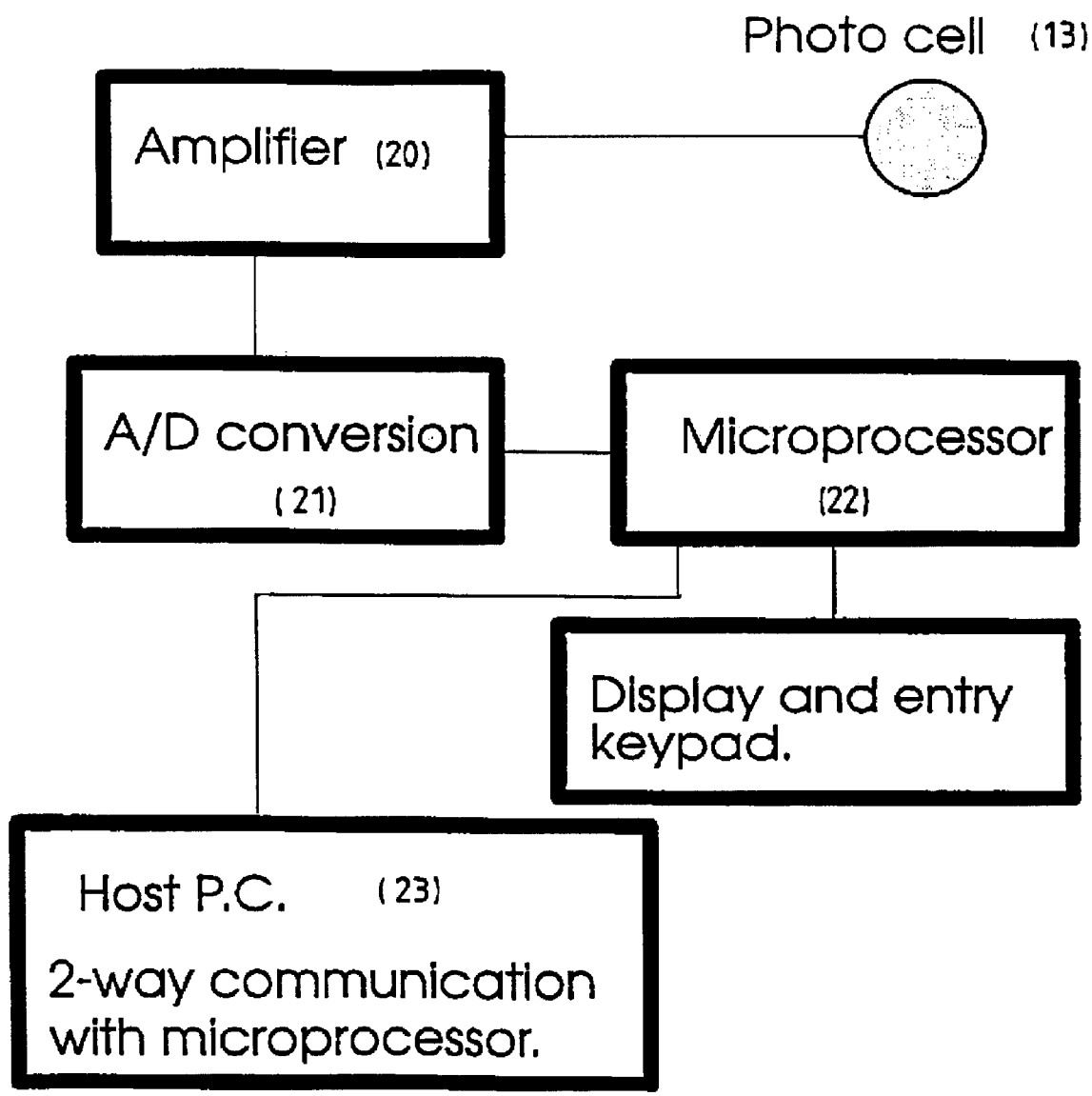
FIG. 4 is a schematic view of system components in an embodiment of the present invention.

With reference to FIGS. 2 through 4, light 15, 16 from different wavelengths (in the infrared range) and at different angles from a series of emitters (11,12) is detected by an optoelectronic photo cell 13 after this light has travelled through the sample 14, or is reflected from the sample. The light is measured on the opposite side to measure primarily absorption, as well as from the same side of the photo cell to measure primarily reflection, of the sample.

The signal from the photo detector 13 is amplified 20 and passed on to an A/D converter 21. The signal is of a pulsed nature since the light sources are triggered in sequence under microprocessor 22 control so that the microprocessor can work out from which light source the signal originates. The speed of sampling and triggering of the lights puts a limit on the speed of fluid travel through the cell. The main bulk of the fluid can travel at speeds of up to 50 cm/second or even more because the cell only grabs a small portion of the sample travelling at a much slower rate (for the arrangement of FIG. 1c)

The information that is now available to the microprocessor 22 is passed on to a host PC 23 through a bus system (bidirectional). The PC receives the information and makes the necessary calculations and comparisons through a local database and sends the result back to the microprocessor 22. The microprocessor now presents this information on a display mounted on the tester.

EXAMPLES 2

Data Handling

EXAMPLE 2a

The data may be treated in a variety of manners. Some typical examples have been discussed generally in preceding sections of this specification. One particular example which may be implemented is as follows.

| No. | Prot. | Fat | 60 | 40 | 20 | 0 | 20 | 40 | 60 | Fat | Prot. | |
|---|---|---|---|---|---|---|---|---|---|---|---|---|
| 1 | 4.04 | 5.28 | 372 | 443 | 215 | 390 | 352 | 305 | 77 | 5.28 | 4.04 | |
| 2 | 4.45 | 6.27 | 361 | 433 | 208 | 375 | 338 | 290 | 72 | 6.27 | 4.45 | |
| 3 | 4.17 | 5.59 | 376 | 449 | 217 | 392 | 355 | 306 | 76 | 5.59 | 4.17 | |
| 4 | 3.92 | 5.42 | 376 | 450 | 217 | 394 | 356 | 307 | 77 | 5.42 | 3.92 | |
| 5 | 4.32 | 5.98 | 383 | 457 | 220 | 398 | 362 | 314 | 79 | 5.98 | 4.32 | |
| 6 | 4.54 | 6.34 | 366 | 438 | 211 | 381 | 343 | 294 | 74 | 6.34 | 4.54 | |
| 7 | 4.38 | 6.39 | 363 | 435 | 210 | 377 | 340 | 290 | 72 | 6.39 | 4.38 | |
| 8 | 3.74 | 5.44 | 383 | 456 | 222 | 401 | 364 | 316 | 79 | 5.44 | 3.74 | |
| 9 | 4.64 | 5.67 | 366 | 437 | 212 | 379 | 342 | 293 | 74 | 5.67 | 4.64 | |
| 10 | 3.93 | 5.35 | 372 | 444 | 214 | 386 | 350 | 301 | 76 | 5.35 | 3.93 | |
| 11 | 4.18 | 5.85 | 367 | 436 | 210 | 380 | 344 | 295 | 74 | 5.85 | 4.18 | |
| 12 | 4 | 5.49 | 382 | 452 | 219 | 400 | 364 | 316 | 80 | 5.49 | 4 | |
| 13 | 4.56 | 6.71 | 352 | 422 | 204 | 365 | 328 | 280 | 72 | 6.71 | 4.56 | |
| 14 | 3.89 | 5.31 | 381 | 451 | 219 | 398 | 361 | 313 | 79 | 5.31 | 3.89 | |
| 15 | 4.39 | 6.25 | 355 | 424 | 204 | 366 | 329 | 281 | 71 | 6.25 | 4.39 | |
| 16 | 5.14 | 7.75 | 342 | 410 | 197 | 352 | 315 | 266 | 68 | 7.75 | 5.14 | |
| 17 | 5.34 | 8 | 341 | 410 | 197 | 350 | 313 | 265 | 67 | 8 | 5.34 | |
| 18 | 4.49 | 5.17 | 386 | 456 | 221 | 402 | 365 | 317 | 81 | 5.17 | 4.49 | |
| 19 | 4.76 | 7.27 | 369 | 439 | 213 | 386 | 349 | 299 | 76 | 7.27 | 4.76 | |
| 20 | 3.93 | 5.44 | 378 | 446 | 216 | 392 | 355 | 306 | 77 | 5.44 | 3.93 | |
| 21 | 4.62 | 6.54 | 367 | 433 | 208 | 377 | 341 | 292 | 74 | 6.54 | 4.62 | egressi |
| 22 | 3.96 | 5.73 | 361 | 427 | 206 | 371 | 335 | 287 | 71 | 5.73 | 3.96 | |
| 23 | 4.41 | 5.94 | 367 | 431 | 208 | 376 | 340 | 290 | 73 | 5.94 | 4.41 | |
| 24 | 3.76 | 5.04 | 382 | 447 | 216 | 393 | 357 | 309 | 78 | 5.04 | 3.76 | |
| 25 | 3.85 | 5.3 | 389 | 455 | 221 | 403 | 366 | 318 | 80 | 5.3 | 3.85 | |
| 26 | 3.93 | 5.45 | 389 | 452 | 218 | 400 | 364 | 314 | 79 | 5.45 | 3.93 | |
| 27 | 4.37 | 5.59 | 381 | 446 | 216 | 392 | 355 | 306 | 78 | 5.59 | 4.37 | |
| 28 | 4.06 | 5.62 | 371 | 435 | 210 | 379 | 343 | 294 | 75 | 5.62 | 4.06 | |
| 29 | 5.02 | 7.8 | 343 | 408 | 196 | 350 | 313 | 265 | 67 | 7.8 | 5.02 | |
| 30 | 4.86 | 7.39 | 346 | 410 | 196 | 351 | 313 | 264 | 67 | 7.39 | 4.86 | |
| 31 | 5.11 | 7.19 | 359 | 422 | 203 | 368 | 330 | 280 | 71 | 7.19 | 5.11 | |
| 32 | 4.2 | 5.89 | 363 | 423 | 203 | 369 | 334 | 287 | 72 | 5.89 | 4.2 | |
| 33 | 4.47 | 6.14 | 352 | 414 | 199 | 356 | 319 | 272 | 69 | 6.14 | 4.47 | |
| 34 | 4.22 | 6 | 358 | 421 | 202 | 363 | 326 | 278 | 71 | 6 | 4.22 | |
| 35 | 5.2 | 7.03 | 359 | 422 | 203 | 365 | 328 | 279 | 71 | 7.03 | 5.2 | |
| 36 | 5.2 | 7.59 | 350 | 417 | 200 | 360 | 322 | 274 | 67 | 7.59 | 5.2 | |
| 37 | 5.16 | 7.91 | 342 | 406 | 195 | 348 | 311 | 263 | 65 | 7.91 | 5.16 | |
| 38 | 4.33 | 6.28 | 346 | 409 | 196 | 351 | 314 | 266 | 66 | 6.28 | 4.33 | |
| 39 | 6.44 | 9.01 | 333 | 396 | 189 | 335 | 298 | 251 | 62 | 9.01 | 6.44 | |
| 40 | 3.92 | 5.27 | 378 | 440 | 211 | 386 | 349 | 299 | 74 | 5.27 | 3.92 | |
| 41 | 4.34 | 5.68 | 373 | 435 | 210 | 381 | 344 | 294 | 76 | 5.68 | 4.34 | |
| 42 | 4.24 | 5.62 | 362 | 422 | 200 | 386 | 364 | 291 | 72 | 5.62 | 4.24 | |
| 43 | 4.22 | 5.62 | 364 | 425 | 205 | 370 | 333 | 284 | 74 | 5.62 | 4.22 | |
| 44 | 4.28 | 5.45 | 369 | 431 | 207 | 376 | 339 | 289 | 75 | 5.45 | 4.28 | |
| 45 | 4.37 | 5.82 | 363 | 424 | 203 | 370 | 332 | 283 | 74 | 5.82 | 4.37 | |
| 46 | 4.35 | 6.01 | 361 | 421 | 202 | 365 | 329 | 280 | 74 | 6.01 | 4.35 | |
| 47 | 4.33 | 5.47 | 369 | 429 | 206 | 375 | 337 | 288 | 75 | 5.47 | 4.33 | |
| 48 | 3.84 | 5.13 | 389 | 449 | 217 | 396 | 359 | 329 | 83 | 5.13 | 3.84 | |
| 49 | 4.31 | 5.73 | 377 | 439 | 212 | 386 | 349 | 299 | 79 | 5.73 | 4.31 | |
| 50 | 5.27 | 7.42 | 346 | 407 | 195 | 350 | 313 | 266 | 70 | 7.42 | 5.27 | |

| Regression Statistics proteins | | | | | | |
|---|---|---|---|---|---|---|
| | | Analysis of Variance | | | | |
| Multiple R | 0.791571 | | df | of Squares | ean Square | F | gnificance F |
| R Square | 0.626585 | Regression | 7 | 8.32371 | 1.189101 | 10.06791 | 2.56E − 07 |
| Adjusted R | 0.564349 | Residual | 42 | 4.96054 | 0.118108 | | |
| Standard Er | 0.343669 | Total | 49 | 13.28425 | | | |
| Observatio | 50 | | | | | | |

| | Coefficients | ndard Error | t Statistic | P-value | Lower 95% | Upper 95% |
|---|---|---|---|---|---|---|
| Intercept | 13.45706 | 3.581796 | 3.757071 | 0.000458 | 6.228704 | 20.68542 |
| x1 | −0.03174 | 0.020854 | −1.52188 | 0.134467 | −0.07382 | 0.010348 |
| x2 | 0.004916 | 0.051169 | 0.09607 | 0.923857 | −0.09835 | 0.108179 |
| x3 | −0.01804 | 0.087539 | −0.20611 | 0.837558 | −0.1947 | 0.158618 |
| x4 | 0.046398 | 0.075203 | 0.61696 | 0.540117 | −0.10537 | 0.198164 |
| x5 | −0.0368 | 0.047914 | −0.76796 | 0.446197 | −0.13349 | 0.059898 |
| x6 | −0.00454 | 0.019881 | −0.22848 | 0.820225 | −0.04466 | 0.035579 |
| x7 | 0.007708 | 0.04608 | 0.167282 | 0.867837 | −0.08528 | 0.100701 |

-continued

| n Statistics | Fat | Analysis of Variance | | | | | |
|---|---|---|---|---|---|---|---|
| | | | df | of Squares | ean Square | F | gnificance F |
| Multiple R | 0.863849 | | | | | | |
| R Square | 0.746236 | Regression | 7 | 31.21069 | 4.45867 | 17.644 | 1.15E − 10 |
| Adjusted R | 0.703942 | Residual | 42 | 10.61347 | 0.252702 | | |
| Standard Er | 0.502695 | Total | 49 | 41.82416 | | | |
| Observatio | 50 | | | | | | |

| | Coefficients | ndard Error | t Statistic | P-value | Lower 95% | Upper 95% |
|---|---|---|---|---|---|---|
| Intercept | 26.63764 | 5.239202 | 5.084293 | 5.79E − 06 | 16.0645 | 37.21078 |
| x1 | −0.07971 | 0.030504 | −2.61313 | 0.011881 | −0.14127 | −0.01815 |
| x2 | −0.01325 | 0.074846 | −0.17707 | 0.860185 | −0.1643 | 0.137793 |
| x3 | 0.002873 | 0.128045 | 0.022436 | 0.982191 | −0.25553 | 0.261279 |
| x4 | 0.097821 | 0.110002 | 0.889263 | 0.378207 | −0.12417 | 0.319815 |
| x5 | −0.07874 | 0.070085 | −1.12355 | 0.26668 | −0.22018 | 0.062694 |
| x6 | 0.025556 | 0.02908 | 0.878811 | 0.383793 | −0.03313 | 0.084242 |
| x7 | −0.05041 | 0.067402 | −0.74785 | 0.458122 | −0.18643 | 0.0856161 |

| 42 | 3.69% | 0.850718 |
|---|---|---|
| 35 | 4.37% | 0.956384 |
| 30 | 1.29% | 0.996797 |
| 25 | 3.88% | 0.894907 |
| 22 | 2.90% | 0.958661 |
| All | 7.16% | 0.863849 |

| | | Analysis of Variance | | | 42 | | |
|---|---|---|---|---|---|---|---|
| Regression Statistics | | | df | of Squares | ean Square | F | gnificance F |
| Multiple R | 0.850718 | Regression | 7 | 1.225702 | 0.1751 | 0.74844 | 0.677522 |
| R Square | 0.723722 | Residual | 2 | 0.467908 | 0.233954 | | |
| Adjusted R | −0.24325 | Total | 9 | 1.69361 | | | |
| Standard Er | 0.483688 | | | | | | |
| Observatio | 10 | | | | | | |

| | Coefficients | ndard Error | t Statistic | P-value | Lower 95% | Upper 95% |
|---|---|---|---|---|---|---|
| Intercept | −12.4148 | 34.10755 | −0.36399 | 0.724269 | −159.168 | 134.3382 |
| x1 | 0.178219 | 0.816792 | 0.218194 | 0.832145 | −3.33616 | 3.692596 |
| x2 | 0.149033 | 0.427439 | 0.348665 | 0.735358 | −1.69009 | 1.988155 |
| x3 | −0.06005 | 0.45407 | −0.13224 | 0.897701 | −2.01375 | 1.893658 |
| x4 | 0.148766 | 0.382993 | 0.388429 | 0.706727 | −1.49912 | 1.796655 |
| x5 | −0.57092 | 0.677014 | −0.8433 | 0.420909 | −3.48388 | 2.342033 |
| x6 | 0.225008 | 0.310678 | 0.724249 | 0.487312 | −1.11173 | 1.561748 |
| x7 | −0.35622 | 0.525343 | −0.67807 | 0.514782 | −2.61659 | 1.904152 |

| | | Analysis of Variance | | | 35 | | |
|---|---|---|---|---|---|---|---|
| Regressing Statistics | | | df | of Squares | ean Square | F | gnificance F |
| Multiple R | 0.956384 | Regression | 7 | 9.104119 | 1.300588 | 3.062656 | 0.268142 |
| R Square | 0.914671 | Residual | 2 | 0.849321 | 0.42466 | | |
| Adjusted R | 0.616018 | Total | 9 | 9.95344 | | | |
| Standard Er | 0.65166 | | | | | | |
| Observatio | 10 | | | | | | |

| | Coefficients | ndard Error | t Statistic | P-value | Lower 95% | Upper 95% |
|---|---|---|---|---|---|---|
| Intercept | −12.0689 | 70.83227 | −0.17039 | 0.868475 | −316.836 | 292.698 |
| x1 | −0.3767 | 0.492808 | −0.7644 | 0.464199 | −2.49708 | 1.743681 |
| x2 | 0.234021 | 0.803534 | 0.29124 | 0.777469 | −3.22331 | 3.691353 |
| x3 | −0.19314 | 1.358684 | −0.14215 | 0.890092 | −6.03909 | 5.652811 |
| x4 | 0.546261 | 1.505394 | 0.362869 | 0.725079 | −5.93093 | 7.023455 |
| x5 | 0.014886 | 1.278153 | 0.011647 | 0.990962 | −5.48457 | 5.51434 |
| x6 | −0.38582 | 0.479663 | −0.80435 | 0.441924 | −2.44964 | 1.678009 |
| x7 | −0.05336 | 0.525545 | −0.10153 | 0.921356 | −2.3146 | 2.20788 |

| | | Analysis of Variance | | | 30 | | |
|---|---|---|---|---|---|---|---|
| Regression Statistics | | | df | of Squares | ean Square | F | gnificance F |
| Multiple R | 0.996797 | Regression | 7 | 7.502514 | 1.071788 | 44.39321 | 0.022204 |
| R Square | 0.993605 | Residual | 2 | 0.048286 | 0.024143 | | |

-continued

| | | Total | 9 | 7.5508 | | |
|---|---|---|---|---|---|---|
| Adjusted R | 0.971223 | | | | | |
| Standard Er | 0.15538 | | | | | |
| Observatio | 10 | | | | | |

| | Coefficients | ndard Error | t Statistic | P-value | Lower 95% | Upper 95% |
|---|---|---|---|---|---|---|
| Intercept | 70.35572 | 17.56148 | 4.006253 | 0.003081 | −5.20528 | 145.9167 |
| x1 | −0.27178 | 0.079898 | −3.40153 | 0.007854 | −0.61555 | 0.071999 |
| x2 | −0.25385 | 0.132902 | −1.91007 | 0.088451 | −0.82569 | 0.31798 |
| x3 | −0.52072 | 0.121766 | −4.27638 | 0.002061 | −1.04464 | 0.003199 |
| x4 | 0.807338 | 0.129986 | 6.21095 | 0.000157 | 0.248052 | 1.366624 |
| x5 | −0.16915 | 0.121916 | −1.38746 | 0.198692 | −0.69372 | 0.35541 |
| x6 | −0.13001 | 0.10778 | −1.20623 | 0.258478 | −0.59375 | 0.333734 |
| x7 | 0.613654 | 0.126007 | 4.870019 | 0.000883 | 0.071491 | 1.155817 |

| | | Analysis of Variance | | 25 | | |
|---|---|---|---|---|---|---|
| Regression Statistics | | | df | of Squares | ean Square | F | gnificance F |

| | | | df | of Squares | ean Square | F | gnificance F |
|---|---|---|---|---|---|---|---|
| Multiple R | 0.894907 | Regression | 7 | 9.17039 | 1.310056 | 1.14902 | 0.54033 |
| R Square | 0.800859 | Residual | 2 | 2.2803 | 1.14015 | | |
| Adjusted R | 0.103866 | Total | 9 | 11.45069 | | | |
| Standard Er | 1.067778 | | | | | | |
| Observatio | 10 | | | | | | |

| | Coefficients | ndard Error | t Statistic | P-value | Lower 95% | Upper 95% |
|---|---|---|---|---|---|---|
| Intercept | 30.2866 | 41.21162 | 0.734904 | 0.481107 | −147.033 | 207.606 |
| x1 | −0.35509 | 0.498777 | −0.71192 | 0.494554 | −2.50115 | 1.790976 |
| x2 | 0.389841 | 0.894871 | 0.435639 | 0.67336 | −3.46048 | 4.240162 |
| x3 | −0.61763 | 1.519435 | −0.40649 | 0.693881 | −7.15524 | 5.919974 |
| x4 | −0.25678 | 1.232546 | −0.20833 | 0.839609 | −5.56 | 5.046445 |
| x5 | 0.906962 | 1.689096 | 0.536951 | 0.60432 | −6.36064 | 8.17456 |
| x6 | −0.55137 | 0.726325 | −0.75912 | 0.467197 | −3.67649 | 2.573759 |
| x7 | 0.207375 | 0.662645 | 0.312951 | 0.761448 | −2.64376 | 3.058506 |

| | | Analysis of Variance | | 22 | | | |
|---|---|---|---|---|---|---|---|
| Regression Statistics | | | df | of Squares | ean Square | F | gnificance F |
| Multiple R | 0.958661 | Regression | 7 | 3.155078 | 0.450725 | 3.242951 | 0.25586 |
| R Square | 0.919031 | Residual | 2 | 0.277972 | 0.138986 | | |
| Adjusted R | 0.635637 | Total | 9 | 3.43305 | | | |
| Standard Er | 0.372808 | | | | | | |
| Observatio | 10 | | | | | | |

| | Coefficients | ndard Error | t Statistic | P-value | Lower 95% | Upper 95% |
|---|---|---|---|---|---|---|
| Intercept | 32.17584 | 18.52941 | 1.736474 | 0.116495 | −47.5498 | 111.9015 |
| x1 | −0.31515 | 0.211498 | −1.49006 | 0.170395 | −1.22515 | 0.594859 |
| x2 | 0.052115 | 0.351606 | 0.14822 | 0.885437 | −1.46073 | 1.564956 |
| x3 | 0.127434 | 0.311164 | 0.409541 | 0.691718 | −1.2114 | 1.466264 |
| x4 | 0.068553 | 0.26027 | 0.26339 | 0.798181 | −1.0513 | 1.188407 |
| x5 | −0.03034 | 0.141157 | −0.21494 | 0.834605 | −0.63769 | 0.57701 |
| x6 | 0.022677 | 0.041903 | 0.541182 | 0.601519 | −0.15762 | 0.202971 |
| x7 | 0.250415 | 0.216929 | 1.154362 | 0.278082 | −0.68296 | 1.183787 |

Figure 5:
FIGS. 5–7 are some graphs of sample data from calibration and test trials, performed using an embodiment of the present invention.
Figure 6:
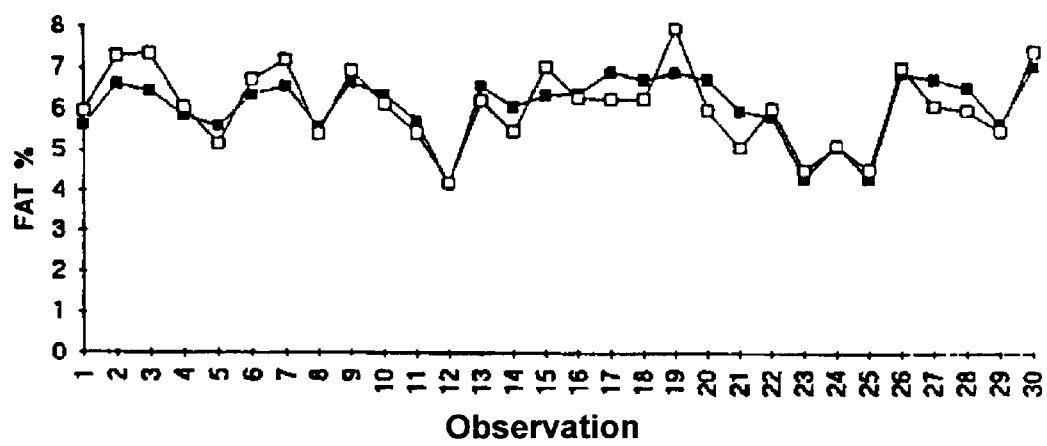

The method is based on measuring the scattered light intensity under different angles I(θ) in the infrared part of the spectrum around 750–1200 nm wavelengths. Afterwards use is made of the multiple regression equation:

$$FAT = \Sigma \alpha_I I(\theta_l) + \alpha_O$$

with the regression coefficients $\alpha_I$ calculated preliminary we will get estimation for the FAT value. From FIG. 5 it can be seen that the predicted values using the above the written regression equation compared to independently measured FAT values are in good agreement. In these preliminary measurements we used only one wavelength. Our calculations show that the error of 8% is observed over the FAT range [4, 8] and an error of 6% is observed in the range [4, 6.5]. This could be explained with the slight dependence of the scattered light intensity on FAT contents in region [6.5, 8] (see FIG. 6) The usage of sets of different wavelength diodes will improve the accuracy of detecting the fat contents. The presence of more data for the different angles (especially angles near to 90° (eg. 70° and 110° though 90°±60° may be an acceptable range for many embodiments)) will make the accuracy of the estimation better.

In use it is considered that most embodiments may be supplied with data characteristic of the fluid samples to be measured. However it is likely that calibration runs will need to be performed before accurate determination runs can be performed. These calibration runs will typically be performed initially, and routinely thereafterwards to check the accuracy of readings against drift and changing parameters.

Such calibration runs may not be performed by the end user but by service personnel at routine inspections.

A detailed description of a particular embodiment trialed by the inventor now follows. This description is by way of example only and is not intended to limit the scope of the invention.

EXAMPLE 2b

Calibration Procedure

The principle of operation relies on a mathematical calculation by a multiple regression method of statistical data. It is therefore necessary to calibrate the cell against one or more known pilot fluids or known reference/test fluid. This fluid is usually a tested milk sample for milk analysis. Testing can of course also be done afterwards.

Accuracy can be calculated by the software, though accuracy and reproducibility is largely determined by the stability of the chosen embodiment. For instance, a change in temperature may affect the reading and a gradual contamination on the surface of the glass walls of the cell may also affect the accuracy of the reading.

Weekly calibration is recommended and as an alternative method the report from the dairy factory on the bulk fat results may be used as a daily pilot check. This can calibrate individual machines to a certain extent in the overall system. Every day after each milking a bulk fat content is worked out by the software.

EXAMPLE 2c

Interpretation of the Data

In the first lot of samples, only 50 samples were run through a measuring cell.

In the graphs of the raw data fat/protein can be seen the seven groups of data together, these are the outputs resulting from the scatter from the 7 LED's in the prototype.

From the observations we can see that the readings are not equally spread over the whole range and that the readings are relatively high compared to average milk. The reason for this is that the samples were collected from factory supply farms in New Zealand, the late autumn period just before drying off the whole herd as well as that the popularity of the Jersey breed of cows. Milk fat readings as high as 9% or even more have been observed (not in this set of data).

There is a clear trend in each group with a downward slope to the right. The slope in the data means that the correlation factor is relatively high and thus the likelihood of more accurate estimation can be expected. Contrary to this in some groups of data points there is a significant deviation from this general slope. This means that the information we get out of that light source under these circumstances contributes a little less to the predicted point than the data that follows the general sloping trend. These points generally give us other information about solids in the milk than the fat alone. This is one of the reasons why I have used more than 1 light source for observation.

After treatment of all data points with a multiple regression method we obtain the correlation factor and the intercept or the free factor in the summation of the formula to obtain the data points we want to calculate.

The result of the predicted value can be obtained by multiplication of each individual reading (raw data) with its own regression coefficient factor and addition of the intercept. This result will closely match the measured fat readings, within the limits given by the relative error from other methods (chemical or calibrated infrared).

Figure 7:
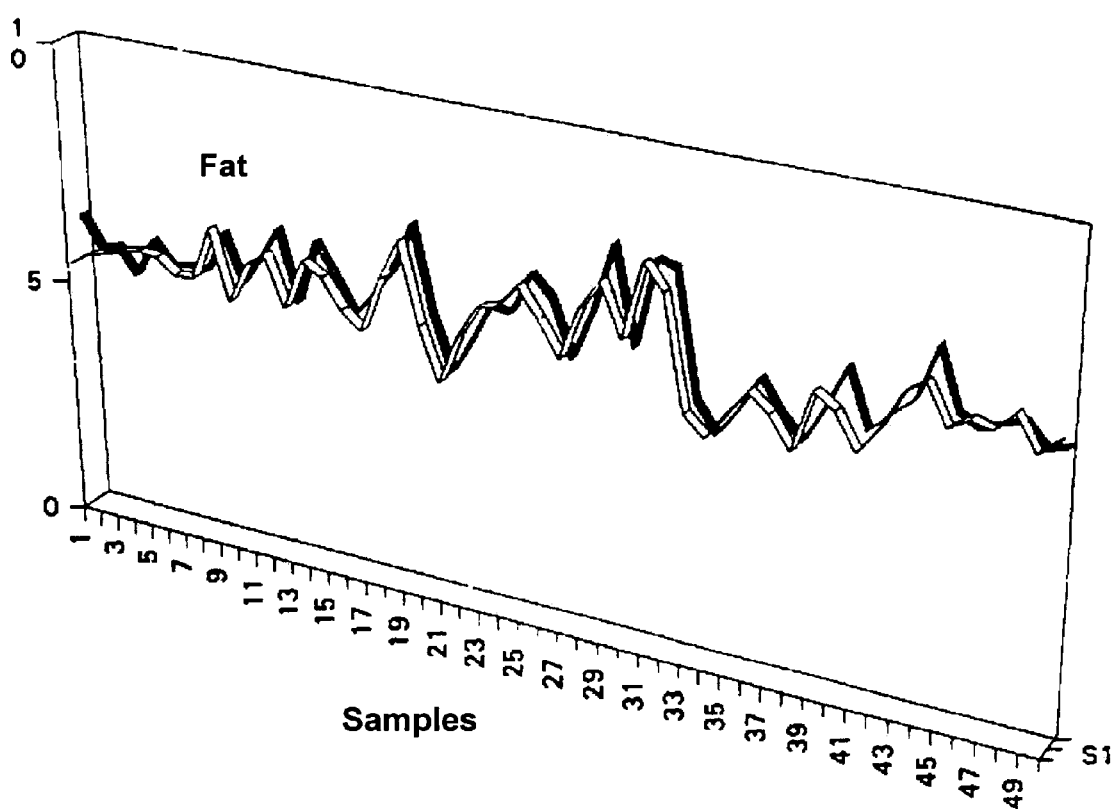

The line plots of both fat and protein (see, for instance, FIG. 7) indicate the good relationship between the predicted and the measured protein and fat readings. In this trial an overall relative accuracy of approximately 5% has been achieved. However, the conditions under which these readings were taken were less than ideal. The temperature dependence (see other results) was not taken into account. The readings were taken at approximately room temperature (we never measured this temperature).

Later work indicated that an increase in temperature to approximately 35° C. resulted in much better correlation, with a relative accuracy better than 2%.

According to our temperature observations the best results were obtained between 30–40° after heating our samples up for approximately 20 minutes in a thermostatically controlled water bath. Fortunately one would normally be dealing with milk straight from the cow which already has this body temperature, and the fat globules/particles will be dissolved under optimum conditions, making measurements more accurate.

We carried out our observations in lots of 10 samples with approximately 5° intervals in temperature. Temperature dependence is obvious, but ideally we need to do more work in this area. From the test results you can see that the error around 30° is only 1.29%. All these results were obtained without many suggested improvements in the physical make up of the test cell. It is clear to us that even better results can be obtained given some more time to fine tune this method.

EXAMPLE 3a

Figure 8:
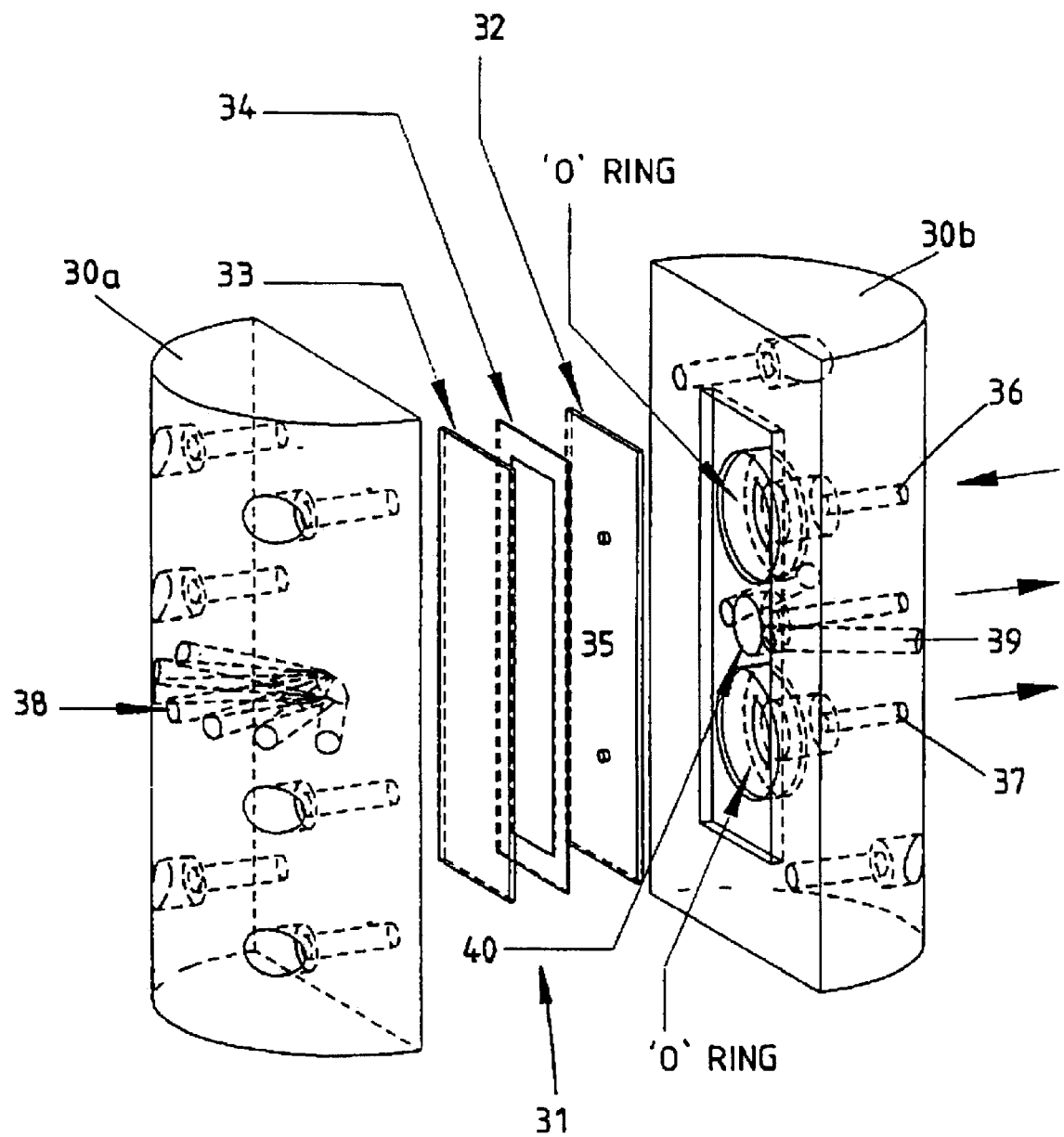
FIG. 8 is an exploded perspective diagrammatic view of a thin-cell embodiment of the present invention.

FIG. 8 illustrates a further embodiment of the present invention. The apparatus comprises two body halves 30a and 30b which sandwich a cell (generally indicated by arrow 31) therebetween. The cell comprises a front 32 and rear 33 optical window with a teflon gasket 34 positioned therebetween. The gasket 34 spaces the windows 32, 33 and defines the thickness of the sample cell. Apertures 35 in the front window 32 allow for the flow of milk or other sample fluids through inlet 36 and outlet 37 channels within the body 30b.

Provided in the rear body half 30a are a plurality of apertures 38 into which the output of light emitters (not shown) may be directed. For LED's 38a these may be positioned directly in the apertures 38. Also provided are some additional apertures 39 on the front body half which may be optionally used for additional emitters (e.g. 39a (again not shown in FIG. 8)). In the context of FIGS. 1, these emitters will be primarily for eliciting a reflectance response from the apparatus.

A detector 40 comprising a photo diode is positioned in front body half 30b substantially as shown. This is connected to an A/D converter or other processing means for evaluating the response.

Figure 9:
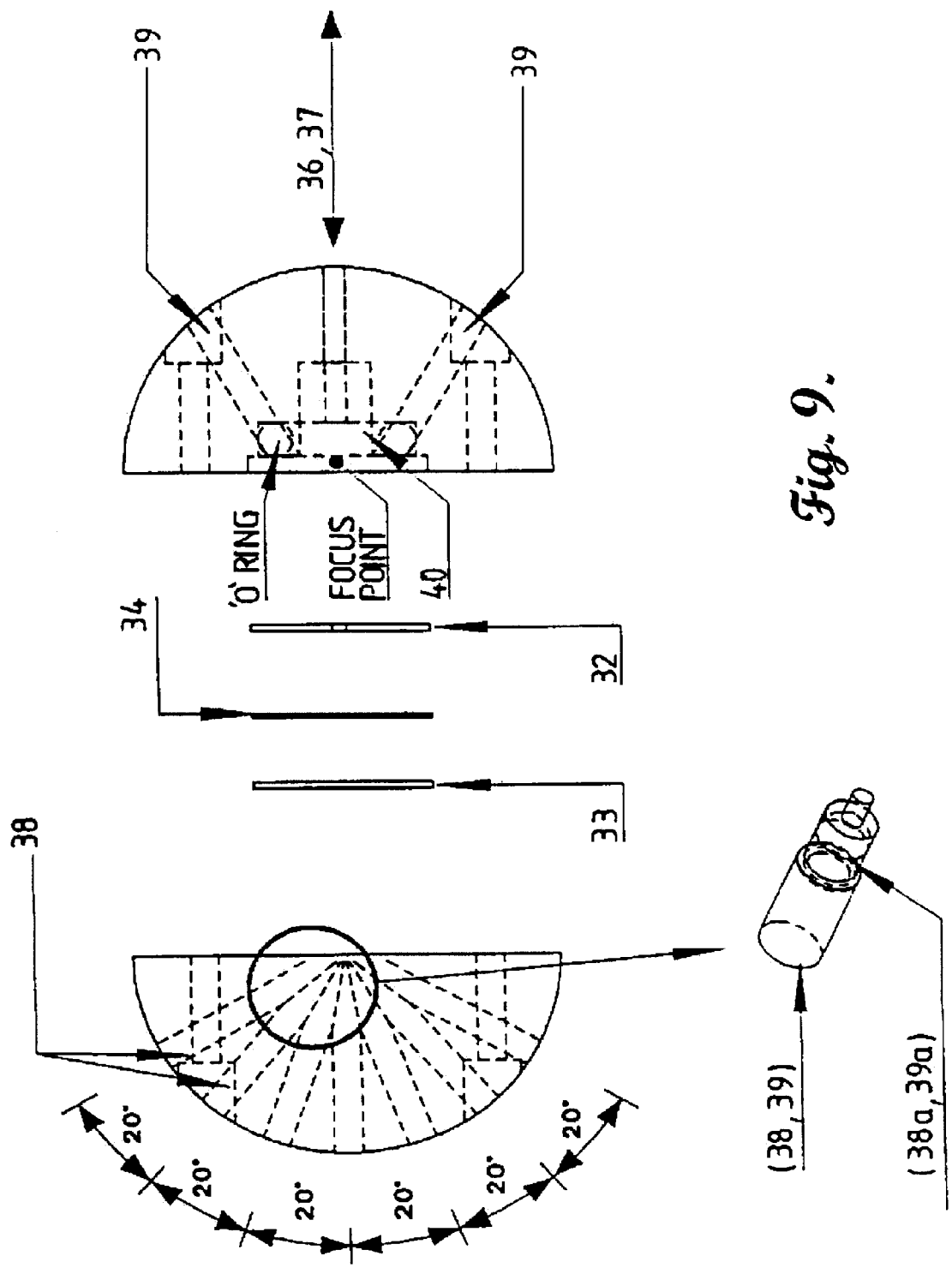
FIG. 9 is a plan diagrammatic view of the embodiment of FIG. 8.
Figure 10:
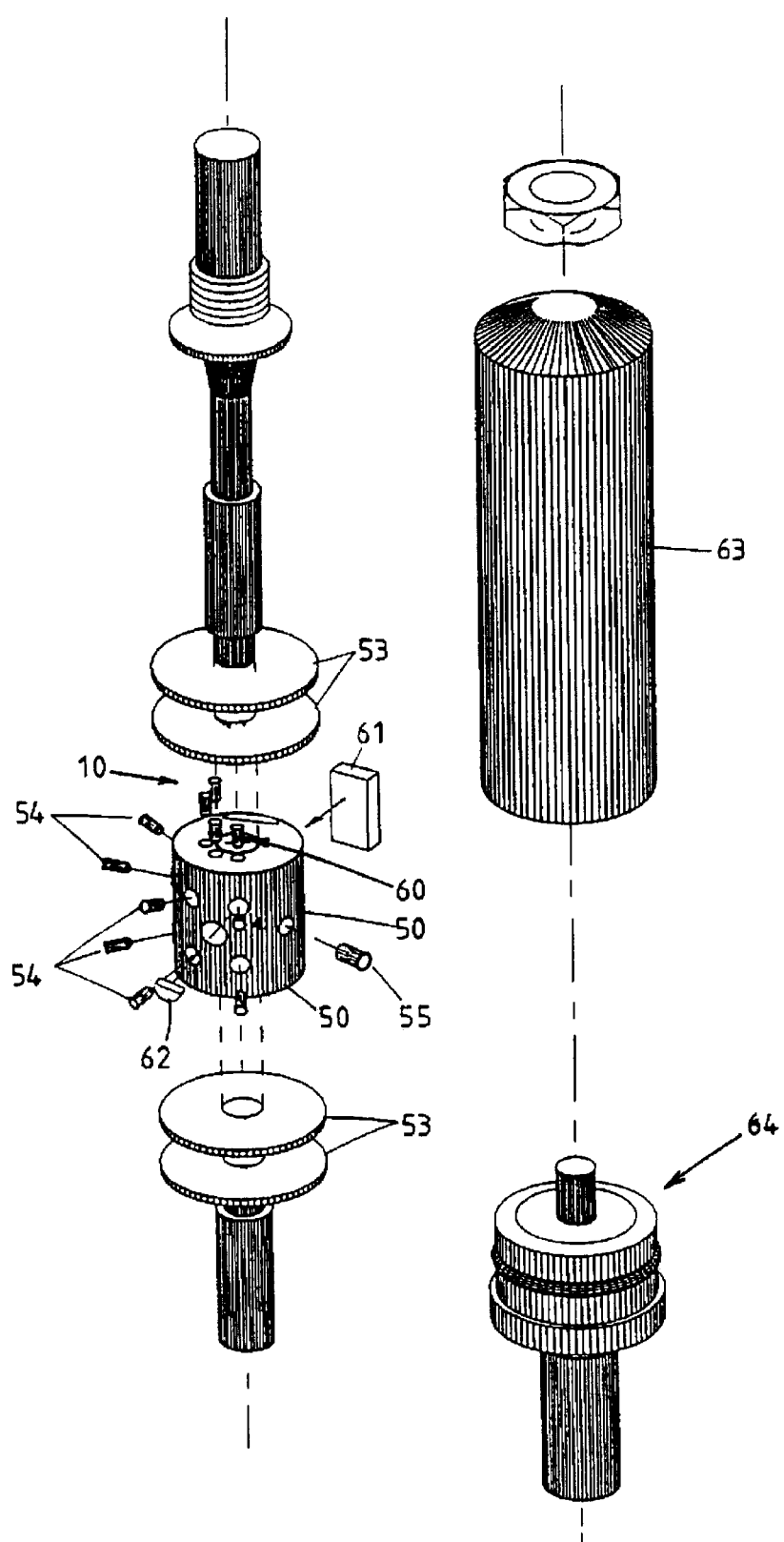
FIG. 10 is an exploded perspective diagrammatic view of a through-flow embodiment of the present invention.
Figure 12:
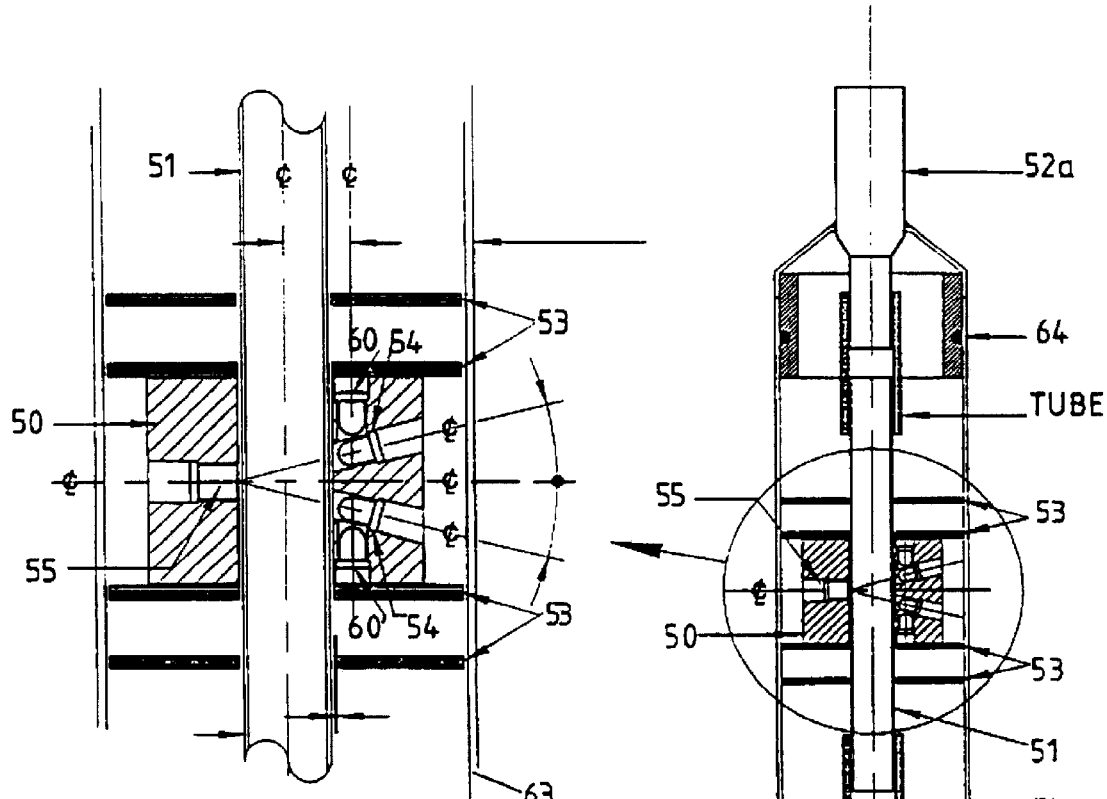
FIG. 12 is an enlarged view of the detecting portion of the illustration of FIG. 11.
Figure 11:
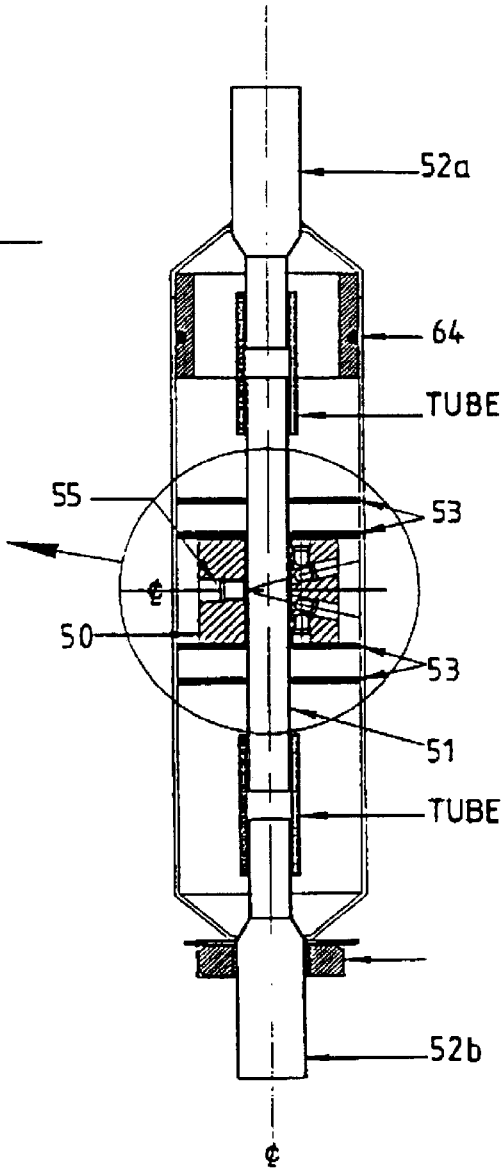
FIG. 11 is a side cross-sectional diagrammatic view of the embodiment of FIG. 10.
Figure 13:
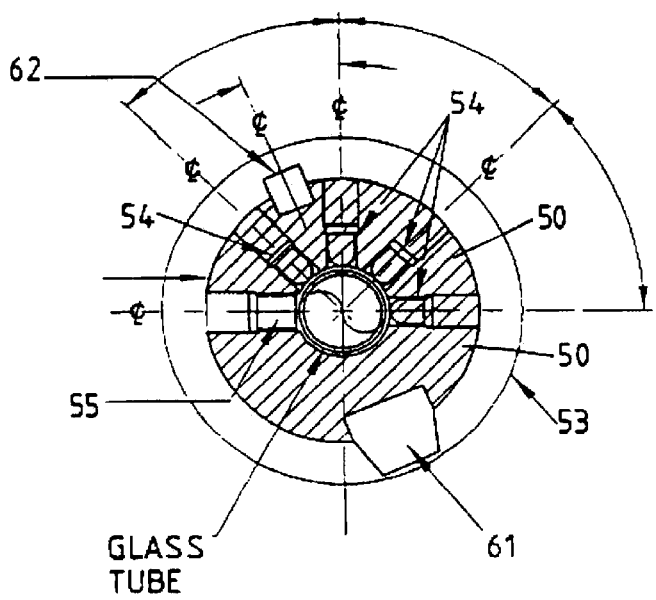
FIG. 13 is a top plan diagrammatic view of the portion shown in FIG. 12.

FIG. 9 represents an alternative view of the embodiment of FIG. 8. It is noted that the embodiment of FIGS. 8 and 9 could be readily modified to accept a sample phial instead of relying upon the illustrated sample cell 31. This would typically mean providing a central aperture of cylindrical shape to accept the phial. Some modifications would need to be made to the body portions (30a, 30b) typically including offsetting the detector further back into body portion 30b. It may also be necessary to adjust the conduits 38 for the optical paths so as to converge substantially on the repositioned detector 40. However. this need not necessarily be accomplished as optical paths which do not converge on the detector 40 will still provide a signal which will be scattered and dispersed by particles within the fluid, providing a reading to the detector 40. In such instances it may not be necessary to provide the reflectance signal paths 39.

EXAMPLE 4

FIGS. 10 through 13 illustrate a further preferred embodiment of the present invention. This embodiment is suitable for analysing a continuous flow of sample material, though may also be adapted to accept a sample cell or phial. The embodiment is also suitable for analysing a wide range of samples, including milk, oils and lubricants, particle presence in gases, blood and biological fluids, etc.

There is provided a body 50 comprising a central aperture through which a glass or silica tube 51 is maintained in place. At each end the sample tube 51 is connected to a sample flow line (52a, 52b by tubing). Housed within the body 50 are the emitters 54 and detectors 55. The arrangement of the emitters 54 (comprising IR emitting LED's) and the detector 55 (comprising a photo diode) are clearly seen in FIGS. 12 and 13.

To improve stability of the apparatus, the body 50 is of a block of material normally having low to medium thermal conductivity and reasonable mass. High density plastics are a preferred choice. In addition a gap is provided between the sample tube 51 and body 50, as well as the circuit boards positioned at either end of same, and the attached components so as to provide thermal isolation from the sample tube 51.

The LED's are arranged in 3-dimensional array. This is perhaps at best seen by referring to FIGS. 12 and 13. In effect there are four sets of emitting LED's (each associated with a detecting LED for feedback purposes—see below) which provide a plurality of different paths through the sample fluid for subsequent detection by the photo diode detector 55. Two LEDs (54) of each set are pulsed and a reading taken by the detector 55 for that particular set. If desired, each individual emitter LED, rather than pair, could also be pulsed individually so as to provide more data for subsequent analysis.

It is also noted that other arrangements of LED's may be relied upon. In a variation of this embodiment (not illustrated) there is provided a plurality of substantially planar arrays of LED's distributed in substantially the arrangement visible in FIG. 13. Each planar set of LED's is coupled to its detector 55, the readings being either averaged for subsequent analysis, or providing separate data for subsequent analysis.

In further variations of this, and other, embodiments fibre optics may be used to channel light from an emitter to one or more points. This can reduce the number of emitters, associated circuitry, and possible problems from different stabilities.

To further assist stability, a further LED 60 is provided for each emitter LED 54. These additional LEDs 60 are of the same type as the emitter LEDs 54 but are configured to act as detectors rather than emitters. These additional LEDs 60 are coupled to the circuitry to alter the voltage and/or current to the emitter LEDs to ensure that their output remains constant and unaffected by variables such as time, temperature etc. Other methods of utilising this optical feedback have been discussed previously and may be employed in variations of this embodiment, and other embodiments of the present invention.

Further, a heater 61 may be thermally coupled to the body 50 to help maintain it at a constant temperature. In this instance it would be desirable that the body 50 did possess some thermal conductivity though a consideration is that it should not be so conductive that rapid changes in the sample are immediately transmitted to cause rapid fluctuations of temperature in the body 50. This could be addressed by providing a heating coil about the block of the body 50 or heating devices distributed throughout. Typically such heating devices 61 would be controlled by one or more temperature sensors 62. Cooling devices (Peltier effect devices being one likely choice) can also be provided for cooling.

Typically the entire assemblage is then contained in an outer housing 63 which protects the internal components. Washers and O-rings 64 may be relied upon to seal the unit.

The output from the detector 55 is then fed to external processing equipment. This may be converted to a digital form by an A/D converter, which could be included within the illustrated sensing device in FIGS. 12 through 14. This can then be analysed as previously discussed in previous examples and description of the specification.

EXAMPLE 4b

The embodiment of FIGS. 10 through 13 will generally be inserted in a position in which it is able to monitor sample fluids. Before analysis can begin, a range of calibration data needs to be obtained for comparison and subsequent evaluation. Typically this is performed by obtaining a set of reference samples which are analysed by the apparatus. The values from the detector would then be recorded and various mathematical transformations performed to allow detector values for unknown samples to be converted into an indication of particle content within that sample.

For the highest degree of accuracy there is some benefit in ensuring that the reference samples are analysed in similar conditions to what a normal fluid sample would be. This will often mean similar physical characteristics, such as the same temperature, the same type of sample cell, and where possible the same flow rate. However it may be difficult to generate this flow for a reference sample—in many embodiments the pulsed nature of the emitters will tend to grab substantially stationary snap shots of the sample which should compare favourably with the reference sample data for most applications of the present invention.

In practice, each sensing device may be calibrated when it leaves the factory and a particular set of data prepared for subsequent evaluation by the evaluation means whenever that sensor is used. In addition, calibration may be routinely performed to compensate for any drift from factory settings, or changes in the conditions by which samples are measured (if they differ from the conditions under which the original factory data was obtained).

For a sample such as milk, it has been found that a variety of different constituents may be measured. For instance, fat content, protein content, somatic cell count, as well as lactose content can all be determined. Generally, for calibration, 50 samples are obtained whose contents of each of the foregoing (or any other component that needs to be analysed), is known. Reference sample may be specifically made up, though the use of milk samples which have been previously analysed, can be used. The data from the 50 samples is then collected and the correlation between the detector output values and the known contents of each component performed. In most cases a good correlation can be obtained, depending upon choosing the right method of correlation e.g. linear regression, Fourier transform (when appropriate) etc.

The mathematical transformation required to convert a detector value into an indication of a particular particle constituent is then recorded for future use with this reference sample.

Similar techniques would also be applied for other types of fluids. For substances such as lubricants, it would not normally be possible to differentiate between different types of metal particles present in the lubricant, though an indication of the metal content as opposed to something like carbon content would typically be possible. The presence of other contaminants which are not dissolved totally within the main lubricant phase (e.g. water) can often also be determined.

Similarly, for many biological samples, there is a range of different substances suspended, or otherwise present in a non-dissolved form, within the fluid. Quite often different particles have different absorption and reflection patterns, which can be distinguished by use of the present invention.

EXAMPLE 4c

Figure 14:
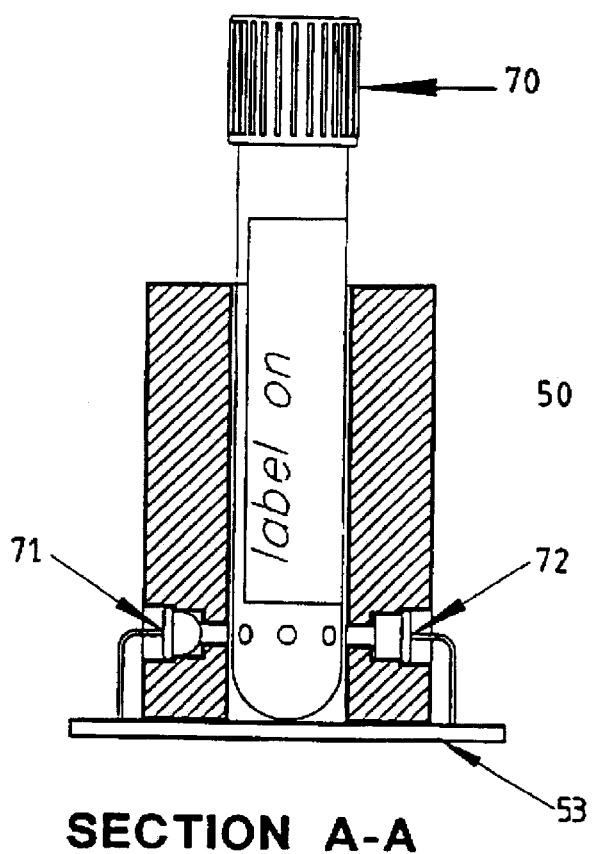
FIG. 14 is a side cross-sectional diagrammatic view of a test-tube accepting embodiment of the present invention.
Figure 15:
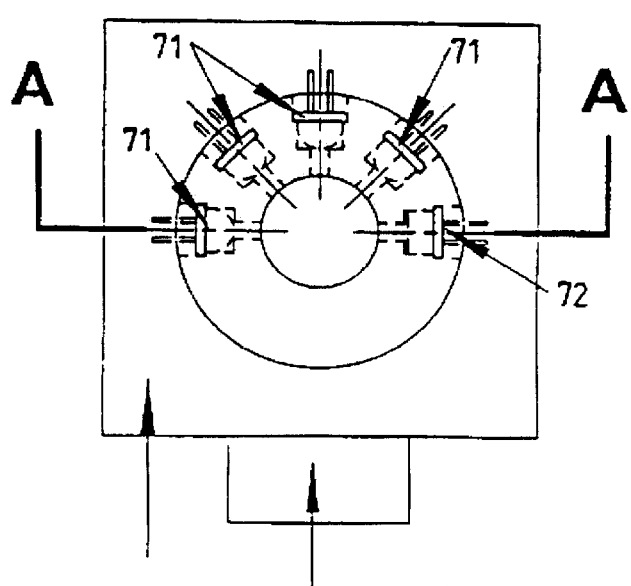
FIG. 15 is a plan diagrammatic view of the embodiment of FIG. 14.

FIGS. 14 and 15 illustrate an alternative embodiment of the present invention directed to use with phials. Analysis of blood products is one application.

The embodiment comprises a body 50 having a central aperture in which a phial 70 can be inserted. A planar array of emitters 71 are provided though other arrangements (see previous examples for instance) may be adopted.

Light signals are detected by detector 72 which is connected to the chosen evaluation/processing means. For convenience the device may be mounted on a circuit board 53 also supporting the other associated componentry.

EXAMPLE 4d

Monitoring Application

Embodiments described thus far have focused primarily on embodiments providing a value indicative of particle content. However many foreseeable applications of the present invention include uses as monitoring equipment to indicate only when particular components have exceeded a predetermined value. In this case the processing and evaluation equipment need not be so sophisticated. Typically the sensor will be calibrated by connection with normal processing equipment, and the particular characteristics of that sensor recorded onto appropriate media (e.g. an EPROM chip) to be included with the sensor. The sensor will also contain some processing equipment to determine whether a detector response exceeds a level exceeding a predetermined value which is equivalent to some limit. For instance, the device could be set to indicate when the water content in a lubricant exceed 0.5%. The device would be adjusted so that a monitoring portion would be triggered when the detector output exceeds a level equivalent to a 0.5% water level. At this point the monitoring circuit may switch or latch to a different state to sound an appropriate alarm or cause some reaction to the event.

It should be appreciated that while digital evaluation is perhaps the most effective method for allowing the various evaluation processes to occur, for a simple monitoring application where only a single comparison is being made as to whether a detector output exceeds a certain level or not, a simple analogue comparison circuit may also be sufficient. This can help reduce the expense though it is envisaged that in most instances the unit will need to be calibrated and adjusted or hooked up to other equipment—which may be the full processing and evaluation equipment such as previously described in other examples, or specialised equipment solely for the task or calibrating sensors for monitor applications.

EXAMPLE 4e

Flowrates

Most embodiments of the present invention can be used with little or no hardware modification for determining flow rates. In a pulsed embodiment, where an emitter is pulsed, 'snapshots' of the sample are taken in rapid succession. If the interval of the snapshot is short enough, one may (depending upon the uniformity of the sample) notice variations between the characteristics of each snapshot of the moving sample. These variations are due to changes in concentration, presence of bubbles, particles and foreign matter etc. If a second (or third etc.) snapshot is taken downstream then comparison may be made by the processing portion/software to match the snapshots and thereby determine the time taken to travel between the two detection sites. As the distance of separation of the detection sites are known, the velocity and hence flow rate of the fluid can be determined.

Knowing the flow rate, whether it be determined in the above manner or by conventional flow measuring techniques, can allow further analysis of the sample to be performed. Determining the flow rate, and thereby establishing a time domain can be useful for analytical techniques such as Fourier Transform analysis.

EXAMPLE 5

Various Other Changes and Improvements

Modifications may be made to various embodiments. Within the infra-red range, certain substances absorb certain wavelengths by varying degrees. In addition, it is also likely that their reflectance will change. The sensitivity of the apparatus to particular substances, some of which may be dissolved, can be improved by including the use of light sources which produce an output at a particular frequency with which a particular substance interacts. Accordingly some of the LEDs or other light sources used may produce light of the wavelengths in this region of interaction. Where a highly sensitive, specific sensor is to be produced, virtually all the light sources may be of this type so as to increase the sensitivity and specificity of the sensor unit. However, for most embodiments it is generally envisaged that it may be useful to include several emitters producing different wavelengths. This allows one to attribute what is occurring because of an interaction at a particular wavelength due to the constituent of interest, rather than from interactions from constituents not of interest in a sample. This aids analysis of different compounds in a single sample.

Aspects of the present invention have been described by way of example only and it should be appreciated that modifications and additions may be made thereto without departing from the scope thereof as defined in the appended claims.

What is claimed is:

1. Apparatus for quantitative particle determination in fluids having a particle content, said apparatus comprising:

an emitter set comprising one or more light emitters, each acting as a point light source, providing one or more sample light signals as output;

a detector set comprising one or more light detectors sensitive to the output of the light emitters, wherein the sample light signals from a plurality of discrete sample light signal paths between the emitter and detector sets are received by the detector set during analysis of a sample, the detector set being operable to discern between different sample light signal paths;

a signal connection adapted for communicating information received from the detector set to a processor for processing one or more values indicative of the presence of particles within a sample fluid; and a feedback detector positioned to receive incident light from an emitter of said emitter set; said feedback detector providing an output used to compensate for any drifting of the emitter's output from a predetermined ideal norm through either or both of:

i) control of the emitter's output, and ii) influencing the sensitivity of at least one light detector to match the light output of said emitter;

the detector set providing, for a plurality of different sample light signal paths, individual output values which can be evaluated by a processor for providing a value indicative of the fluid particle content of the fluid sample being analyzed.

2. Apparatus as claimed in claim 1 in which the detector set is arranged to detect at least one set of scattered or reflected light signals due to reflectance by particles present within the fluid.

3. Apparatus as claimed in claim 1 in which said feedback detector influences:

either or both the voltage and current of at least one light emitter whose directly incident light it detects to maintain the emitter light output at a predetermined level.

4. Apparatus as claimed in claim 3, in which said feedback detector comprises a light emitter of substantially the same type and characteristics as the light emitter whose output it monitors.

5. Apparatus as claimed in claim 1 in which said sample light signal paths differ from each other by at least one of:

a path length through the fluid sample being analyzed, and a relative path angle through the fluid sample being analyzed.

6. Apparatus as claimed in claim 1 in which one or more sample light signals are within the infrared region of the electromagnetic spectrum.

7. Apparatus as claimed in claim 6 in which one or more sample light signals have a wavelength in the regions 750–1200 nm or 3000–10000 nm.

8. Apparatus as claimed in claim 1 in which a light emitter comprises a light emitting diode (LED).

9. Apparatus as claimed in claim 1 in which a light detector comprises a photo diode, light emitting diode (LED), photo transistor, or other opto-electronic device.

10. Apparatus as claimed in claim 1 wherein said emitter set comprises a plurality of light emitters at different positions along a wall or walls of a sample cell, or positioned to be present along a wall or walls of an inserted sample cell.

11. Apparatus as claimed in claim 10 in which said emitters are arranged in a substantially radial manner about a substantially curved sample cell, or cell holder.

12. Apparatus as claimed in claim 10, in which there is provided a plurality of groups of emitter set and detector set pairs, each group of emitter and detector sets functioning substantially independently of other groups and the output of each detector set being considered by a processor when providing a value indicative of particle presence within the fluid sample being analyzed.

13. Apparatus as claimed in claim 1 in which the output of at least one light emitter is pulsed during analysis of a sample fluid.

14. Apparatus as claimed in claim 13 comprising aplurality of pulsed light emitters, and in which the detector set, or an individual detector of the detector set, detects substantially the output of a single light emitter, or combination thereof, at a time during analysis of a sample fluid; the pulsing of said light emitters being synchronised to allow the detection of the output of individual light emitters, or groups thereof.

15. Apparatus as claimed in claim 1 in which the output of at least one light emitter is varied in its output intensity during analysis of a sample fluid.

16. Apparatus as claimed in claim 15 in which the detector set, or an individual detector of the detector set, produces a signal available for evaluation by a processor at more than one output intensity of said light emitter(s).

17. Apparatus as claimed in claim 1 in which at least one detector of the detector set is positioned and operated to receive at least one signal during analysis of a sample fluid which comprises purely reflected or scattered light, and not directly transmitted light, from one or more emitters of the emitter set.

18. Apparatus as claimed in claim 1 in which the output of the detector set is converted to a digital format.

19. Apparatus as claimed in claim 18 in which data is prepared into packets which is available to a processer for evaluation in producing a value indicative of particle presence within a sample fluid.

20. Apparatus as claimed in claim 1 which includes a processer for producing one or more values indicative of the presence of particles within a sample fluid.

21. Apparatus as claimed within claim 20 in which said processor compares values produced by the detector set with stored calibration reference values, the comparison producing values indicative of the presence of one or more different types of particles within a sample fluid.

22. Apparatus as claimed in claim 21 in which the stored values comprise calibration data relating to chosen standards.

23. Apparatus as claimed in claim 22 in which the comparison of data is based on either or both linear regression or Fourier transformations.

24. Apparatus as claimed in claim 1 which includes, or is configured to include, a sample cell capable of allowing a continuous flow of sample therethrough.

25. Apparatus as claimed in claim 1 which is connected to a milk line.

26. Apparatus as claimed in claim 1 which is connected to an oil line.

27. Apparatus as claimed in claim 1 which is connected to a lubricant line.

28. Apparatus as claimed in claim 1, wherein said feedback detector also provides an output whose value can be evaluated by a processor when providing a value indicative of the fluid particle content.

29. A method of quantitative determination of the levels of one or more different particles in a fluid comprising:

i) transmitting one or more light signals as output from one or more emitters into a fluid sample wherein the emitters act as point light sources;

ii) detecting the light signals from a plurality of different discrete sample light signal paths as output with one or more detectors, wherein different discrete sample light signal paths are discernable one from the other; and ii) making the detected output for each discrete sample light signal path available for subsequent evaluation by a processor;

wherein an output value is obtained from a feedback detector positioned to receive incident light from at least one emitter, the output value being used as a correction for drift in the output of said emitter by either or both of i) control of the emitter's output, and ii) influencing the sensitivity of at least one light detector to match the light output of said emitter.

30. A method as claimed in claim 29 in which the detected light signals differ by at least one of the following:

a path length through the fluid sample being analyzed;

a relative path angle through the fluid sample being analyzed;

the output intensity of the emitter producing said signal;

the proportion of transmitted to reflected or scattered light, and wavelength.

31. A method as claimed in claim 29 in which the detected output is compared by either or both of linear regression, and Fourier transform analysis, with stored calibration reference values to produce values indicative of the quantitative levels of one or more different types of particles within said fluid.

32. A method as claimed in claim 31 in which the operation of different emitter(s) and detector(s) are co-ordinated to allow the collection of light signals from different combinations thereof.

33. A method as claimed in claim 29 in which the light signals are pulsed.

34. A method as claimed in claim 29 wherein at least one light signal comprises light within the infrared portion of the electromagnetic spectrum.

35. A method as claimed in claim 29 for the determination of particle levels in at least one of:

milk and other dairy based fluids;

substances containing fluidised fat particles, globules, and suspensions;

blood, plasma, semen, urine and other biological fluids;

oils and lubricants, and inks, paints, and liquid pigments.

36. A method as claimed in claim 35 when applied to milk and other dairy based fluids, the method being used to indicate the levels of at least one of: fat, protein, lactose, and somatic cell count.

37. A method of determining the flow rate of a fluid flowing in a conduit from a first position to a second position at a defined distance downstream therefrom, comprising:

(i) performing the method of claim 29 to provide a quantitative determination of the level of one or more particles at the said first position at a start time;

(ii) at said second position, repeating the method of claim 29 and recording a stop time when the said quantitative determination of the level of one or more particles of step (i) is obtained; and (iii) calculating an elapsed time between the said start and stop times and using said elapsed time and said defined distance between the first and second positions to determine the flow rate.

38. Apparatus for particle determination in fluids, said apparatus including:

an emitter set comprising a plurality of light emitters, each received in a conduit providing an optical path convergent at a common focus point, each acting as a point light source, providing one or more light signals as output;

a detector set comprising one or more light detectors sensitive to the output of the light emitters, wherein said common focus point is substantially on a said one of said light detectors, and wherein the sample light signals from a plurality of discrete sample light signal paths between the emitter and the detector sets are received by the detector set during analysis of a sample, the detector set being operable to discern between different sample light signal paths;

the apparatus including compensation for any drifting of an emitter's output from a predetermined ideal norm;

the detector set providing, for a plurality of different sample light signal paths, individual output values which can be evaluated by a processor for providing a value indicative of the fluid particle count.

* * * * *